(12) United States Patent
Wu et al.

(10) Patent No.: US 11,066,378 B2
(45) Date of Patent: Jul. 20, 2021

(54) CAFFEIC ACID DERIVATIVES FOR ANTI-ANGIOGENESIS

(71) Applicants: Taipei Medical University, Taipei (TW); China Medical University, Taichung (TW)

(72) Inventors: Chieh-Hsi Wu, Taipei (TW); Yueh-Hsiung Kuo, Taichung (TW); Chun-Hsu Pan, Taipei (TW)

(73) Assignees: Taipei Medical University, Taipei (TW); China Medical University, Taichung (TW)

( * ) Notice: Subject to any disclaimer, the term of this patent is extended or adjusted under 35 U.S.C. 154(b) by 0 days.

(21) Appl. No.: 14/730,430

(22) Filed: Jun. 4, 2015

(65) Prior Publication Data

US 2016/0355493 A1 Dec. 8, 2016

(51) Int. Cl.
*C07D 307/80* (2006.01)
*A61K 45/06* (2006.01)
*A61K 31/343* (2006.01)

(52) U.S. Cl.
CPC .......... *C07D 307/80* (2013.01); *A61K 31/343* (2013.01); *A61K 45/06* (2013.01)

(58) Field of Classification Search
CPC .............................. C07D 307/80; A61K 45/06
See application file for complete search history.

(56) References Cited

FOREIGN PATENT DOCUMENTS

WO         WO9906388        *    2/1999

OTHER PUBLICATIONS

Han, H. "Targeted Prodrug Design to Optimize Drug Delivery." AAPS Pharmsci. (2000), vol. 2 (1) article 6, pp. 1-11.*
Ettmayer, P., et al. "Lessons Learned from Marketed and Investigational Prodrugs." J. Med. Chem. (2004) 47(10), pp. 2393-2404.*
Testa, B. "Prodrug research: futile or fertile?" Biochem. Pharm. (2004) 68, pp. 2097-2106.*
WebMD. "Caffeic Acid." ©2016. Available from: <http://www.webmd.com/vitamins-supplements/ingredientmono-1266-caffeic%20acid.aspx?activeingredientid=1266&activeingredientname=caffeic%20acid >.*
National Cancer Institute. "Angiogenesis Inhibitors." © 2011. Available from: <http://www.cancer.gov/about-cancer/treatment/types/immunotherapy/angiogenesis-inhibitors-fact-sheet >.*
The Free Dictionary. "Alkene." © 2016. Available from: <http://www.thefreedictionary.com/Alkenyl>.*
The Free Dictionary. "Alkyne." © 2016. Available from: <http://www.thefreedictionary.com/Alkenyl>.*
Yang, Z., et al. "Regioselective Introduction of Carbon-3 Substituents to 5-Alkyl-7-methoxy-2-phenylbenzo[b]furans: Synthesis of a Novel Adenosine A1 Receptor Ligand and Its Derivatives." J. Org. Chem. (1992), vol. 57, No. 26, pp. 7248-7257.*
Kuo, Y., et al. "Synthesis of 5-(3-Hydroxypropyl)-7-methoxy-2-(3'-methoxy-4'-hydroxyphenyl)-3-benzo[b]furancarbaldehyde, a Novel Adenosine A1 Receptor Ligand from the Root of Salvia miltiorrhiza." J. Nat. Prod. (1996), vol. 59, pp. 625-628.*
Kuroda, K., et al. "Analytical pyrolysis of lignin: Products stemming from β-5 substructures." Organic Geochemistry. (2006), vol. 37, pp. 665-673.*
Maeda, S., et al. "Studies on the Preparation of Bioactive Lignans by Oxidative Coupling Reaction. I. Preparation and Lipid Peroxidation Inhibitory Effect of Benzofuran Lignans Related to Schizotenuins." Chem. Pharm. Bull. (1994), vol. 42 (12), pp. 2500-2505.*
Zhou, Z., et al. "Bioactive Benzofuran Neolignans from Aristolochia fordiana." Planta Med. (2013), vol. 79, pp. 1730-1735.*
Chen, L., et al. "Salvinal, a Novel Microtubule Inhibitor Isolated from Salvia miltiorrhizae Bunge (Danshen), with Antimitotic Activity in Multidrug-Sensitive and -Resistant Human Tumor Cells." Molecular Pharmacology. © 2004. vol. 65, No. 1, pp. 77-84.*
Pan, C., et al. "K20E, exhibits anti-angiogenic activities." Toxicology and Applied Pharmacology. (2015), vol. 282, pp. 215-226. (Year: 2015).*
Miert, Sabine Van, et al. "Antileishmanial activity, cytotoxicity and QSAR analysis of synthetic dihydrobenzofuran lignans and related benzofurans." Bioorg. Med. Chem. (2005), vol. 13, pp. 661-669. (Year: 2005).*
Lungcancer.org. "Non-Small Cell Lung Cancer Treatment." (Dec. 2012). Accessed Sep. 17, 2018. Available from: < https://www.lungcancer.org/find_information/publications/163-lung_cancer_101/269-non-small_cell_lung_cancer_treatment >. (Year: 2012).*
Berge, S. "Pharmaceutical Salts." J. Pharmaceutical Sciences. (Jan. 1977), vol. 66, No. 1, pp. 1-19. (Year: 1977).*
Fan, Hua-Fang, et al. "Synthesis and cytotoxicity of novel benzofuran neolignan derivatives." Journal of Chemical Research. (Apr. 2010), pp. 233-235. (Year: 2010).*
Pan, C., et al. "K20E, exhibits anti-angiogenic activities." Toxicology and Applied Pharmacology. (Dec. 4, 2014), vol. 282, pp. 215-226. (Year: 2014).*
Apers et al. (2002) "Antiangiogenic Activity of Synthetic Dihydrobenzofuran Lignans," J. Nat. Prod. 65(5):718-720.
Apers et al. (2003) "Lignans and neolignans as lead compounds," Phytochemistry Reviews. 2(3):201-217.
Office Action corresponding to Taiwanese Patent Application No. 104118239, dated Mar. 23, 2016—English translation of the Search Report and English summary only.

\* cited by examiner

*Primary Examiner* — John S Kenyon
(74) *Attorney, Agent, or Firm* — WPAT, P.C., Intellectual Property Attorneys; Anthony King

(57) ABSTRACT

The present invention develops a series of methyl caffeate derivatives having biological activity in anti-angiogenesis. The present invention suggests that the compounds of the invention possess inhibiting angiogenesis through regulation of VEGF/VEGFR-2 and its downstream signaling cascades in the vascular endothelial cells (VECs).

5 Claims, 14 Drawing Sheets

CAFFEIC ACID DERIVATIVES FOR ANTI-ANGIOGENESIS

FIELD OF THE INVENTION

The present invention relates to compounds, compositions and methods for treating angiogenic disorders. Particularly, the present invention relates to caffeic acid derivatives and their anti-angiogenesis applications.

BACKGROUND OF THE INVENTION

The world health statistics (GLOBOCAN 2008) released by the International Agency for Research on Cancer (IARC) indicated that cancer is still a leading cause of death worldwide. Cellular properties of genomic instability and high mutation rate let tumor cells easily evade (or resist) standard chemotherapy as compared to the normal cells. It has been demonstrated that the pathological progression of angiogenesis was not only involved in the tumor growth but also metastasis of the cancer cells, thus it has become a potential target and therapeutic strategy for cancer targeting therapy. Therefore, vascular endothelial cells (VECs) have been raised as a candidate therapeutic target for applying on cancer therapy because they play a crucial role in tumor induced angiogenesis.

Caffeic acid, an abundant phytochemical exist in many daily natural foods, has been demonstrated to reveal many beneficial biological activities, such as anti-inflammatory and anti-viral effects as well as antioxidation (Touaibia, M., Jean-Francois, J., Doiron, J., 2011. *Caffeic Acid, a versatile pharmacophore: an overview.* Mini-Rev. Med. Chem. 11, 695-713). However, caffeate is easily oxidized in air and slightly soluble in water. These limitations make it difficult to apply as a medical drug. Thus, more and more researchers pay attention on the caffeate derivatives to explore their possible bioactive effects and mechanisms. Sodium caffeate, a stable sodium salt of caffeate, was the first caffeate derivative to be reported with antitumor effect through activating the intrinsic pathway of apoptosis (Xu, F., Zhang, S. H., Shao, R. G., Zhen, Y S., 2005. *Anticancer activity of sodium caffeate and its mechanism.* Acta Pharmacol. Sin. 26, 1248-1252). Besides, its anti-angiogeneic effects were reported by inducing growth inhibition and apoptosis in the endothelial cells (Xu, F., Ou-Yang, Z. G., Zhang, S. H., Song, D. Q., Shao, R. G., Zhen, Y S., 2006. *Sodium caffeate induces endothelial cell apoptosis and inhibits VEGF expression in cancer cells.* Yao Xue Xue Bao. 41, 572-576). Methyl caffeate, a naturally occurring ester of caffeic acid, and its oxidative derivative have been mentioned to be more effective than sodium caffeate in anti-cancer activity (Bailly, F., Toillon, R. A., Tomavo, O., Jouy, N., Hondermarck, H., Cotelle, P., 2013. *Antiproliferative and apoptotic effects of the oxidative dimerization product of methyl caffeate on human breast cancer cells.* Bioorg. Med. Chem. Lett. 23, 574-578). US 20020188021 provides a method of potentiating radiation therapy in a subject in need thereof comprises administering a potentiating agent such as caffeic acid phenethyl ester (CAPE) or an analog thereof to the subject in an amount effective to potentiate radiation therapy in the subject. US 20070232668 provides compounds displaying potency as inhibitors of Jak2/STAT3 pathways and downstream targets and inhibit the growth and survival of cancerous cell lines. US 20100010002 relates to the use of caffeic acid or a derivative or a salt thereof in the treatment of chronic myeloid leukemia (CML) that is resistant to treatment with GLEEVEC (Glivec, Imatinib mesylate or STI571) or for reducing the growth or proliferation of cells that are resistant to GLEEVEC. US 20110275577 provides caffeic acid analog compounds and compositions and their application as pharmaceuticals for the treatment of dermatologic, gynecologic, and genital diseases such as inflammatory dermatologic conditions, dysplasia, neoplasia, in situ carcinoma, invasive carcinoma, lichen sclerosus, lichen planus, vaginal dysplasia, vaginal carcinoma, vulvar dysplasia, vulvar carcinoma, cervical dysplasia, cervical carcinoma, and Kaposi's sarcoma.

However, there still exists a need for an improved caffeic acid derivative and method for treating proliferative disorders.

SUMMARY OF THE INVENTION

The present invention provides a compound having the following formula (I) or (II),

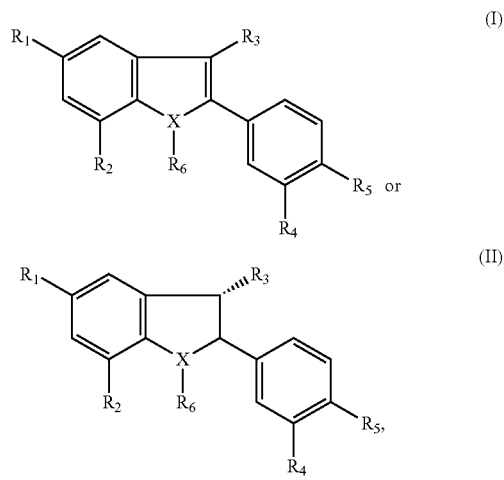

wherein $R_1$, $R_2$, $R_3$, $R_4$, $R_5$ and $R_6$ are defined as described herein.

The present invention also provides a composition comprising the compound of the invention.

The present invention also provides a method for treating disorders and diseases associated with excessive and/or abnormal angiogenesis, comprising administering a compound of the invention to a subject. In some embodiment, the angiogenic disorders include, but not limited to, cancer, diabetic retinopathy, ischemic retinal-vein occlusion, and retinopathy of prematurity, age-related macular degeneration (AMD), neovascular glaucoma, psoriasis, retrolental fibroplasias, angiofibroma, inflammation, rheumatoid arthritis (RA), restenosis, in-stent restenosis, vascular graft restenosis, etc.

BRIEF DESCRIPTION OF THE DRAWING

FIG. 7 shows effects of K20E on the protein levels of p53 and p21 proteins in the HUVECs. The protein expressions were examined by using immunoblot. *P<0.05 compared to the control group (treated with 5% FBS alone).

DETAILED DESCRIPTION OF THE INVENTION

Figure 1A:
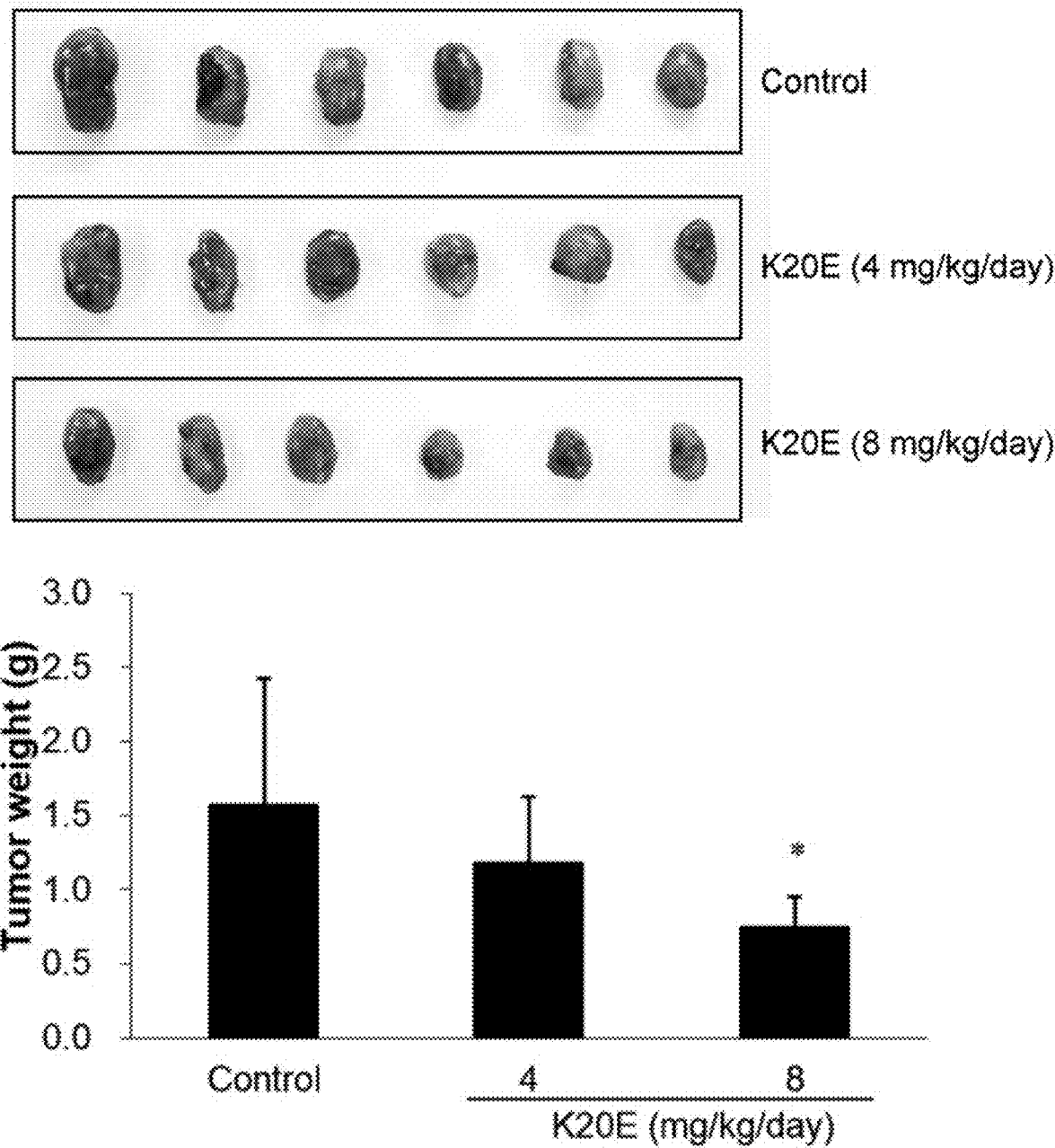
FIGS. 1A-B show inhibitory activities of K20E on tumor growth and angiogenesis. The tumor-bearing mice model (FIG. 1A) and the Matrigel plug assay (FIG. 1B) were applied to evaluate the in vivo activities of K20E in antitumor and anti-angiogenesis, respectively. *P<0.05 and **P<0.01 compared to the control group, respectively. ‡P<0.01 compared to the group treated with VEGF only.

The present invention develops a series of methyl caffeate derivatives having biological activity in anti-angiogenesis. The present invention suggests that the compounds of the invention possess inhibiting angiogenesis through regulation of VEGF/VEGFR-2 and its downstream signaling cascades in the vascular endothelial cells (VECs).

Terms not specifically defined herein should be given the meanings that would be given to them by one of skill in the art in light of the disclosure and the context. As used in the specification, however, unless specified to the contrary, the following terms have the meaning indicated and the following conventions are adhered to.

The terms "a" and "an" refer to one or more.

As used herein, except where the context requires otherwise, the term "comprise" and variations of the term, such as "comprising," "comprises" and "comprised" are not intended to exclude other additives, components, integers or steps.

As used herein, the term "subject" is defined herein to include animals such as mammals, including, but not limited to, primates (e.g., humans), cows, sheep, goats, horses, dogs, cats, rabbits, rats, mice and the like. In specific embodiments, the subject is a human. The terms "subject" and "patient" are used interchangeably herein in reference, for example, to a mammalian subject, such as a human.

As used herein, the terms "treat," "treating" and "treatment" refer to the eradication or amelioration of a disease or disorder, or of one or more symptoms associated with the disease or disorder. In certain embodiments, the terms refer to minimizing the spread or worsening of the disease or disorder resulting from the administration of one or more prophylactic or therapeutic agents to a subject with such a disease or disorder. In some embodiments, the terms refer to the administration of a compound or dosage form provided herein, with or without one or more additional active agent(s), after the diagnosis or onset of symptoms of the particular disease.

As used herein, the terms "prevent," "preventing" and "prevention" refer to the prevention of the onset, recurrence or spread of a disease or disorder, or of one or more symptoms thereof. In certain embodiments, the terms refer to the treatment with or administration of a compound or an antibody or dosage form provided herein, with or without one or more other additional active agent(s), prior to the onset of symptoms, particularly to patients at risk of disease or disorders provided herein. The terms encompass the inhibition or reduction of a symptom of the particular disease. In this regard, the term "prevention" may be interchangeably used with the term "prophylactic treatment.

As used herein, the terms "co-administration" and "in combination with" include the administration of two or more therapeutic agents simultaneously, concurrently or sequentially within no specific time limits unless otherwise indicated. In one embodiment, the therapeutic agents are in the same composition or unit dosage form. In other embodiments, the therapeutic agents are in separate compositions or unit dosage forms.

As used herein, the term "effective amount" is the quantity of compound in which a beneficial outcome is achieved when the compound is administered to a subject or alternatively, the quantity of compound that possess a desired activity in-vivo or in-vitro. In the case of inflammatory disorders and immune disorders, a beneficial clinical outcome includes reduction in the extent or severity of the symptoms associated with the disease or disorder and/or an increase in the longevity and/or quality of life of the subject compared with the absence of the treatment. The precise amount of compound administered to a subject will depend on the type and severity of the disease or condition and on the characteristics of the subject, such as general health, age, sex, body weight and tolerance to drugs. It will also depend on the degree, severity and type of inflammatory disorder. The skilled artisan will be able to determine appropriate dosages depending on these and other factors.

As used herein, the term "alkyl" means a saturated straight chain or branched non-cyclic hydrocarbon typically having from 1 to 6 carbon atoms. Representative saturated straight chain alkyls include methyl, ethyl, n-propyl, n-butyl, n-pentyl and n-hexyl; while saturated branched alkyls include isopropyl, sec-butyl, isobutyl, tert-butyl, isopentyl, 2-methylbutyl, 3-methylbutyl, 2-methylpentyl, 3-methylpentyl, 4-methylpentyl, 2,3-dimethylbutyl etc, and the like.

Alkyl groups included in compounds of this invention may be optionally substituted with one or more substituents, such as amino, alkylamino, alkoxy, alkylthio, oxo, halo, acyl, nitro, hydroxyl, cyano, aryl, alkylaryl, aryloxy, arylthio, arylamino, carbocyclyl, carbocycloxy, carbocyclylthio, carbocyclylamino, heterocyclyl, heterocycloxy, heterocylamino, heterocyclylthio, and the like. In addition, any carbon in the alkyl segment may be substituted with oxygen, sulfur, or nitrogen.

The term "alkoxy," as used herein, refers to an alkyl group which is linked to another moiety though an oxygen atom. Alkoxy groups can be substituted or unsubstituted.

As used herein, the term "alkenyl" means a straight chain or branched, hydrocarbon radical typically having from 2 to 10 carbon atoms and having at least one carbon-carbon double bond. Representative straight chain and branched alkenyls include vinyl, allyl, 1-butenyl, 2-butenyl, isobutylenyl, 1-pentenyl, 2-pentenyl, 3-methyl-1-butenyl, 1-methyl-2-butenyl, 2,3-dimethyl-2-butenyl, 1-hexenyl, 2-hexenyl, 3-hexenyl, 1-heptenyl, 2-heptenyl, 3-heptenyl, 1-octenyl, 2-octenyl, 3-octenyl, 1-nonenyl, 2-nonenyl, 3-nonenyl, 1-decenyl, 2-decenyl, 3-decenyl and the like. Alkenyl groups can be substituted or unsubstituted.

As used herein, the term "alkynyl" means a straight chain or branched, hydrocarbon radical typically having from 2 to 10 carbon atoms and having at least one carbon-carbon triple bond. Representative straight chain and branched alkynyls include acetylenyl, propynyl, 1-butynyl, 2-butynyl, 1-pentynyl, 2-pentynyl, 3-methyl-1-butynyl, 4-pentynyl, -1-hexynyl, 2-hexynyl, 5-hexynyl, 1-heptynyl, 2-heptynyl, 6-heptynyl, 1-octynyl, 2-octynyl, 7-octynyl, 1-nonynyl, 2-nonynyl, 8-nonynyl, 1-decynyl, 2-decynyl, 9-decynyl and the like. Alkynyl groups can be substituted or unsubstituted.

As used herein, the term "alkoxy" refers to the group —O-alkyl (in some embodiments, including from 1 to 10 carbon atoms), of a straight, branched, cyclic configuration and combinations thereof, attached to the parent molecular structure through an oxygen. Examples include methoxy, ethoxy, propoxy, isopropoxy, cyclopropyloxy, cyclohexyloxy, and the like. "Lower alkoxy" refers to alkoxy groups containing one to six carbons. In some embodiments, $C_1$-$C_4$ alkoxy is an alkoxy group which encompasses both straight and branched chain alkyls of from 1 to 4 carbon atoms. Unless stated otherwise in the specification, an alkoxy group is optionally substituted by one or more substituents. The terms "alkenoxy" and "alkynoxy" mirror the above description of "alkoxy" wherein the prefix "alk" is replaced with "alken" or "alkyn" respectively, and the parent "alkenyl" or "alkynyl" terms are as described herein.

The term "substituted" as used herein, means that any one or more hydrogens on the designated atom, radical or moiety is replaced with a selection from the indicated group, provided that the atom's normal valence is not exceeded, and that the substitution results in an acceptably stable compound.

The phrase "pharmaceutically acceptable" is employed herein to refer to those compounds, materials, compositions, and/or dosage forms which are, within the scope of medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like.

As used herein, the term "stereoisomer" is a general term for all isomers of individual molecules that differ only in the orientation of their atoms in space. It includes enantiomers and isomers of compounds with more than one chiral center that are not mirror images of one another (diastereoisomers).

The term "chiral center" refers to a carbon atom to which four different groups are attached.

The terms "enantiomer" and "enantiomeric" refer to a molecule that cannot be superimposed on its mirror image and hence is optically active wherein the enantiomer rotates the plane of polarized light in one direction and its mirror image compound rotates the plane of polarized light in the opposite direction.

The term "racemic" refers to a mixture of equal parts of enantiomers and which mixture is optically inactive.

In one aspect, the present invention provides a compound having the following formula (I) or (II),

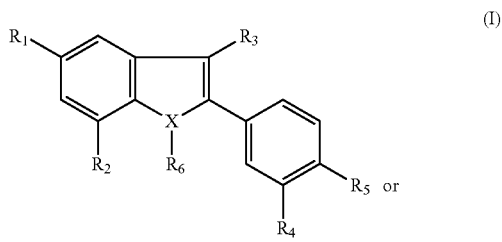

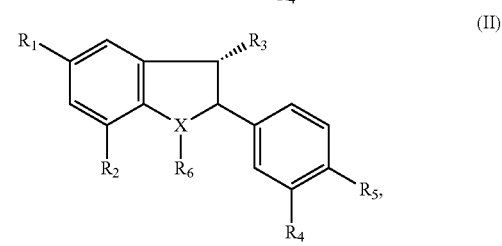

wherein

X is O, N, or S;

$R_1$ is $C_{1-10}$alkyl, $C_{2-10}$alkenyl or $C_{2-10}$alkynyl, unsubstituted or substituted by halogen, $NH_2$, $NO_2$, CN, OH, —CHO, $C(O)_2$C1-10alkyl, $C(O)_2$C1-10alkenyl or $C(O)_2$C1-10alkynyl;

$R_2$ is $C_{1-10}$alkoxy, $C_{2-10}$alkenyloxy, $C_{2-10}$alkynyloxy, —O-acetyl, hydroxy, formyl, halide, CN, $NO_2$, SH, $NH_2$, amido, sulfonyl, or sulfonamido;

$R_3$ is $C_{1-10}$alkyl, $C_{2-10}$alkenyl, $C_{2-10}$alkynyl, $C(O)_2C_{1-10}$alkyl, $C(O)_2C_{1-10}$alkenyl or $C(O)_2$C1-10alkynyl;

$R_4$ is $C_{1-10}$alkoxy, $C_{2-10}$alkenyloxy, $C_{2-10}$alkynyloxy, —O-acetyl, hydroxy, formyl, halide, CN, $NO_2$, SH, $NH_2$, amido, sulfonyl, or sulfonamido;

$R_5$ is OH, $C_{1-10}$alkoxy, $C_{2-10}$alkenyloxy, $C_{2-10}$alkynyloxy, —O-acetyl, hydroxy, formyl, halide, CN, $NO_2$, SH, $NH_2$, amido, sulfonyl, or sulfonamido; and $R_6$ is H, halogen, OH, $NH_2$, CN or $NO_2$;

or a stereoisomer thereof, or an enantiomer thereof, or a prodrug thereof or a pharmaceutically acceptable salt thereof.

In one embodiment, $R_1$ is $C_{1-4}$alkyl or $C_{1-4}$alkenyl unsubstituted or substituted by OH, —CHO or $C(O)_2C_{1-4}$alkyl. In one embodiment, $R_2$ is $C_{1-4}$alkoxy or —O-acetyl. In one embodiment, $R_3$ is $C_{1-4}$alkyl or $C(O)_2C_{1-4}$alkyl. In one embodiment, $R_4$ is $C_{1-4}$alkoxy or —O-acetyl. In one embodiment, R5 is OH or —O-acetyl. In one embodiment, $R_6$ is H.

In some embodiment, $R_1$ is —CH$_2$CH$_2$CH$_2$OH or —CH=CHCHO or —CH=CHC(O)$_2$CH$_3$; $R_2$ is —OCH$_3$ or —O—C(O)CH$_3$; $R_3$ is —CH$_3$ or —C(O)$_2$CH$_3$; $R_4$ is —OCH$_3$ or —O—C(O)CH$_3$; R5 is OH or —O—C(O)CH$_3$; and $R_6$ is H.

In some embodiments, the compound of the invention is selected from the group consisting of:

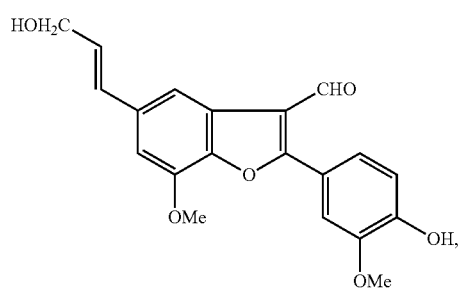
K20

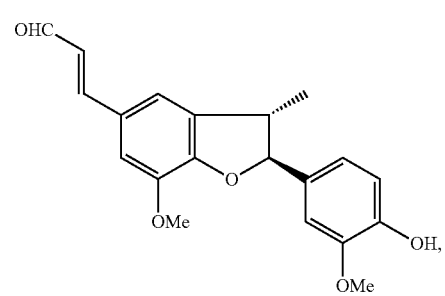
K20A

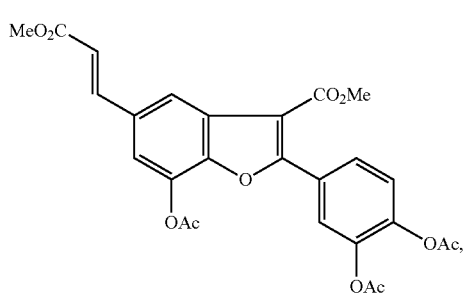
K20B

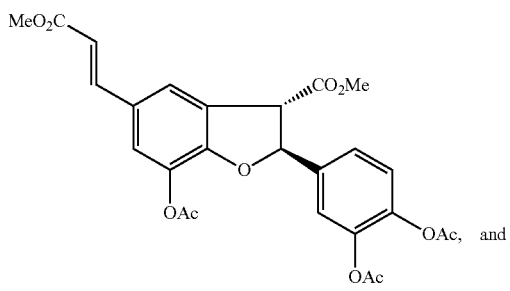
K20E

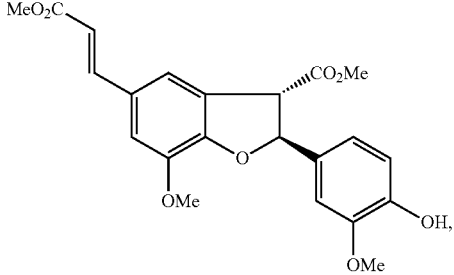
K20L or a stereoisomer thereof, or an enantiomer thereof, or a prodrug thereof or a pharmaceutically acceptable salt thereof.

Isolation and purification of the chemical entities and intermediates described herein can be effected, if desired, by any suitable separation or purification procedure, such as, for example, filtration, extraction, crystallization, column chromatography, thin-layer chromatography, or thick-layer chromatography, or a combination of these procedures. Specific illustrations of suitable separation and isolation procedures are given by reference to the examples herein below. However, other equivalent separation or isolation procedures can also be used.

When desired, the (R)- and (S)-isomers of the non-limiting exemplary compounds, if present, can be resolved by methods known to those skilled in the art, for example by formation of diastereoisomeric salts or complexes which can be separated, for example, by crystallization; via formation of diastereoisomeric derivatives which can be separated, for example, by crystallization, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. Alternatively, a specific enantiomer can be synthesized by asymmetric synthesis using optically active reagents, substrates, catalysts or solvents, or by converting one enantiomer to the other by asymmetric transformation. Further, atropisomers (i.e., stereoisomers from hindered rotation about single bonds) of compounds provided herein can be resolved or isolated by methods known to those skilled in the art.

The compounds described herein can be optionally contacted with a pharmaceutically acceptable acid to form the corresponding acid addition salts. Also, the compounds described herein can be optionally contacted with a pharmaceutically acceptable base to form the corresponding basic addition salts.

In some embodiments, compounds provided herein can generally be synthesized by an appropriate combination of generally well known synthetic methods. Techniques useful in synthesizing these chemical entities are both readily apparent and accessible to those of skill in the relevant art, based on the instant disclosure. Many of the optionally substituted starting compounds and other reactants are commercially available, e.g., from Aldrich Chemical Company (Milwaukee, Wis.) or can be readily prepared by those skilled in the art using commonly employed synthetic methodology.

The discussion below is offered to illustrate certain of the methods available for use in making the following representative compounds and is not intended to limit the scope of reactions or reaction sequences that can be used in preparing the compounds provided herein. The compounds other than the representative compounds are prepared in analogous fashion, which can be understood by modification of the following schemes according to general knowledge and techniques.

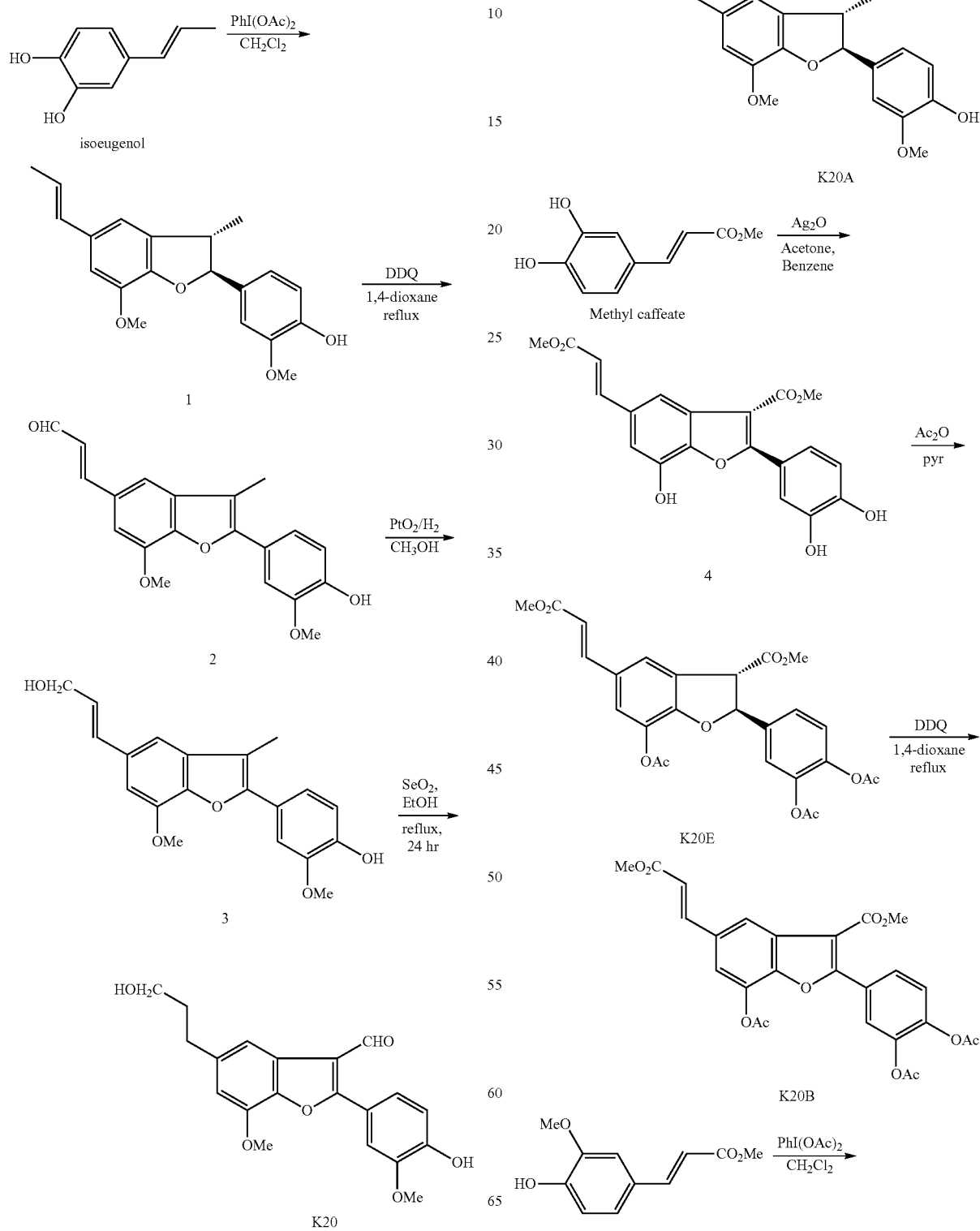

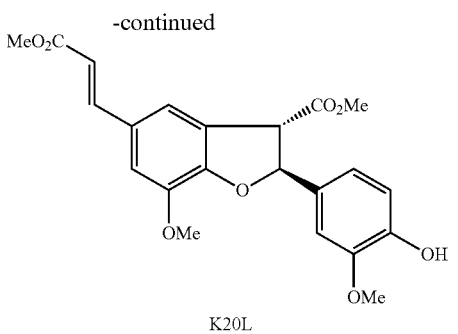

K20L

In another aspect, the invention provides a composition comprising a compound or a stereoisomer, tautomer, salt, or prodrug provided herein. The compositions can be used, for example, in the methods of use described herein.

In another further aspect, the invention provides a method for treating disorders and diseases associated with excessive and/or abnormal angiogenesis, comprising administering a compound of the invention to a subject. Inappropriate and ectopic expression of angiogenesis can be deleterious to an organism. A number of pathological conditions are associated with the growth of extraneous blood vessels. The invention develops to inhibit angiogenic signaling for the purpose treating cancer and angiogenic disorders. The angiogenic disorders include, but not limited to, cancer, diabetic retinopathy, ischemic retinal-vein occlusion, and retinopathy of prematurity, age-related macular degeneration (AMD), neovascular glaucoma, psoriasis, retrolental fibroplasias, angiofibroma, inflammation, rheumatoid arthritis (RA), restenosis, in-stent restenosis, vascular graft restenosis, etc. In addition, the increased blood supply associated with cancerous and neoplastic tissue, encourages growth, leading to rapid tumor enlargement and metastasis. Moreover, the growth of new blood and lymph vessels in a tumor provides an escape route for renegade cells, encouraging metastasis and the consequence spread of the cancer. Thus, compounds of the present invention can be utilized to treat and/or prevent any of the aforementioned angiogenesis disorders, e.g., by inhibiting and/or reducing blood vessel formation; by inhibiting, blocking, reducing, decreasing, etc. endothelial cell proliferation or other types involved in angiogenesis, as well as causing cell death or apoptosis of such cell types. Preferably, the angiogenic disorder is a cancer; more preferably, the cancer is a metastatic cancer; more preferably, the cancer is the cancer is a bladder, blood, bone, bone marrow, brain, breast, colon, esophagus, eye, gastrointestinal, gum, head, kidney, liver, lung, nasopharynx, neck, ovary, prostate, skin, stomach, testis, tongue, eye cancer (such as ocular melanoma), or uterus cancer.

In one embodiment, the method of the invention further comprises administering a second anticancer therapy. Preferably, the second anticancer therapy is chemotherapy, surgical therapy, immunotherapy, or radiation therapy.

In certain embodiments, a composition is a pharmaceutical composition or a single unit dosage form. Pharmaceutical compositions and single unit dosage forms comprise a therapeutically effective amount of a compound of the invention, and optionally a typically one or more pharmaceutically acceptable carriers or excipients or diluents. The carriers and excipients described herein are merely exemplary and are in no way limiting. Suitable carriers or excipients are well-known to those skilled in the art of pharmacy, and non-limiting examples of suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Whether a particular excipient is suitable for incorporation into a pharmaceutical composition or dosage form depends on a variety of factors well known in the art including, but not limited to, the way in which the dosage form will be administered to a patient and the specific active ingredients in the dosage form. The composition or single unit dosage form, if desired, can also contain minor amounts of wetting or emulsifying agents, or pH buffering agents.

Optimal doses may generally be determined using experimental models and/or clinical trials. The optimal dose may depend upon the body mass, weight, or blood volume of the subject. In general, the amount of a compound of described herein, that is present in a dose, ranges from about 0.1 mg to about 10 mg per kg weight of the subject; preferably, about 0.5 mg/kg to about 10 mg/kg, about 0.5 mg/kg to about 8 mg/kg, about 0.5 mg/kg to about 6 mg/kg, about 0.5 mg/kg to about 5 mg/kg, about 1 mg/kg to about 10 mg/kg, about 1 mg/kg to about 8 mg/kg, about 1 mg/kg to about 6 mg/kg, about 1 mg/kg to about 5 mg/kg or about 1 mg/kg to about 3 mg/kg. Subjects may generally be monitored for therapeutic effectiveness using assays suitable for the condition being treated or prevented, which assays will be familiar to those having ordinary skill in the art and are described herein.

The dose of a composition comprising a compound described herein may depend upon the subject's condition, that is, stage of the disease, function, severity of symptoms caused, general health status, as well as age, gender, and weight, and other factors apparent to a person skilled in the medical art. Similarly, the dose of the compound for treating a disease or disorder may be determined according to parameters understood by a person skilled in the medical art. Accordingly, the appropriate dose may depend upon the subject's condition, that is, stage of the disease, general health status, as well as age, gender, and weight, and other factors considered by a person skilled in the medical art.

A pharmaceutical composition may be a sterile aqueous or non-aqueous solution, suspension or emulsion, which additionally comprises a physiologically acceptable excipient (pharmaceutically acceptable or suitable excipient or carrier) (i.e., a non-toxic material that does not interfere with the activity of the active ingredient). Such compositions may be in the form of a solid, liquid, or gas (aerosol). Alternatively, compositions described herein may be formulated as a lyophilizate, or compounds may be encapsulated within liposomes using technology known in the art. Pharmaceutical compositions may also contain other components, which may be biologically active or inactive. Such components include, but are not limited to, buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, stabilizers, dyes, flavoring agents, and suspending agents and/or preservatives.

The compositions can also be formulated as pills, capsules, granules, or tablets which contain, in addition to a compound of the invention, diluents, dispersing and surface active agents, binders, and lubricants. One skilled in this art may further formulate the compound of the invention in an appropriate manner, and in accordance with accepted practices, such as those disclosed in Remington's Pharmaceutical Sciences, Gennaro, Ed., Mack Publishing Co., Easton, Pa. 1990.

Pharmaceutical compositions may be administered in a manner appropriate to the disease or disorder to be treated as determined by persons skilled in the medical arts. An appropriate dose and a suitable duration and frequency of administration will be determined by such factors as the condition of the patient, the type and severity of the patient's disease, the particular form of the active ingredient, and the method of administration. In general, an appropriate dose (or effective dose) and treatment regimen provides the composition(s) comprising a compound as described herein in an amount sufficient to provide therapeutic and/or prophylactic benefit (for example, an improved clinical outcome, such as more frequent complete or partial remissions, or longer disease-free and/or overall survival, or a lessening of symptom severity or other benefit as described herein).

The pharmaceutical compositions described herein that comprise a compound of the invention may be administered to a subject in need by any one of several routes that effectively deliver an effective amount of the compound. Such administrative routes include, for example, topical, oral, nasal, intrathecal, rectal, vaginal, intraocular, subconjunctival, sublingual or parenteral administration, including subcutaneous, intravenous, intramuscular, intrasternal, intracavernous, intrameatal or intraurethral injection or infusion.

The compounds of the present invention suppress the tumor growth in the allograft tumor model and exhibited anti-angiogenic activity. Besides, these compounds significantly reduce arrest of cell cycle at G2/M phase and induce apoptosis. Cell migration, invasion, and tube formation are also markedly suppressed by these compounds. Furthermore, they largely down-regulate the intracellular and secreted vascular endothelial growth factor (VEGF) in cancer cells. Besides, VEGF receptor-2 (VEGFR-2) and its downstream signaling cascades (AKT-mTOR and MEK1/2-ERK1/2) as well as gelatinases are all evidently reduced in cancer cells treated with the compounds of the invention. Inversely, these compounds can up-regulate the expression levels of p53 and p21 proteins in cancer cells.

EXAMPLE

Materials and Methods

Chemicals

The primary antibodies against VEGFR-2 (#9698), phospho-MEK1/2 (#9121), phospho-ERK1/2 (#4370 s), ERK1/2 (#9102), phospho-AKT (#4060), AKT (#9272), phospho-mTOR (#2971), mTOR (#2972), and MMP-2 (#9272) were purchased from the Cell signaling Technology (Beverly, Mass., USA). Anti-MMP-9 (#ab38898) and anti-p21 (#ab7960) antibodies and methyl caffeate (#ab142321) were obtained from the Abcam (Cambridge, Mass., USA). The primary antibodies for detecting MEK1/2 (#sc-6250), VEGF (#sc-7269), and β-actin (#sc-47778) were bought from the Santa Cruz Biotechnology (Santa Cruz, Calif., USA). The primary antibody for detecting p53 (#GTX 100446) was purchased from the GeneTex Inc. (Irvine, Calif., USA). All other reagents that are not mentioned were also purchased from the Sigma-Aldrich (Louis, Mo., USA).

Cell Culture

Human umbilical vein endothelial cells (HUVECs; #8000) were purchased from the ScienCell Research Laboratories (San Diego, Calif., USA). The cells were seeded on gelatin-coated culture dishes and grown in the commercial endothelial cell medium (#1001; ScienCell) containing 5% fetal bovine serum (FBS; #0025; ScienCell), 30 μg/mL endothelial cell growth supplements (ECGS; #1052; ScienCell), 100 units/mL penicillin G, and 100 μg/mL streptomycin sulfates (#0503; ScienCell). Cells at passage 3-6 were used for experiments. Mouse Lewis lung carcinoma cell line 1 (LLC1; #60050) was bought from the Food Industry Research and Development Institute (Hsinchu, Taiwan) and cultured in Gibco® Dulbecco's modified Eagle's medium (#12800-017; Invitrogen, Carlsbad, Calif., USA) supplemented with 10% FBS (HyClone, Logan, Utah, USA), 4 mM L-glutamine, 1.5 g/L sodium bicarbonate, 100 units/mL penicillin G, and 100 μg/mL streptomycin. All cells were incubated in a humidified 5% CO2 atmosphere at 37° C. and culture media was changed every 2~3 days.

Cell Viability Assay (MTT Assay)

The experiments were performed according to our previous study with minor modifications (Pan et al., 2010). Briefly, the cells (2×104 cells/well) were seeded and grown under normal culture medium for 24 h. After another 24 h of starvation with 0.5% FBS, the cells were treated with several concentrations (1, 2, 4, 8, and 16 μM) of the tested compounds for 24 h and then incubated with 5 mg/mL of MTT (3-[4,5-dimethyl thiazol-2-yl]-2,5-diphenyl tetrazolium bromide) for 2 h. After that, the cells were washed with 1×PBS and then dimethyl sulfoxide (DMSO) was added to each well. Absorbance values at 570 nm were determined for each well using 650 nm as the reference wavelength. The absorbance of the control group (treated with 5% or 10% FBS alone) was defined as 100%.

Lewis Lung Carcinoma-Bearing Mouse Model

The experimental design and procedure according to the method reported by our previous study with minor modification (Liu et al., 2013). Briefly, male C57BL/6 mice (average of 8-week-old) were purchased from the BioLASCO (Taipei, Taiwan) and housed in a 12-h light/dark cycles with free access to food and water. All animal care followed the institutional animal ethical guidelines of ChinaMedical University (Taichung, Taiwan). After 1 week adaptation, the mice were divided randomly into three groups (n=6/group): Group 1 (control group; treatment with normal saline), Group 2 (treatment with 4 mg/kg body weight/day of K20E), and Group 3 (treatment with 8 mg/kg body weight/day of K20E). At first, the LLC1 lung cancer cells (6×105 cells in 100 μL of total volume) were injected subcutaneously into the back skin of mice to induce lung carcinoma xenografts. Two weeks later, the tumor-bearing mice began to receive the treatments according to experiment design (normal saline or K20E with different dosages) by intraperitoneal injection once a day for two weeks. At the end of the study, the tumor masses were harvested to photograph and weighted.

Matrigel Plug Assay

Male C57BL/6 (average of 6-week-old) mice were divided randomly into four groups (n=3/group): Group 1 (control group; injection with 500 μL cold-Matrigel [#356237; BD Biosciences]), Group 2 (injection with 500 μL cold-Matrigel containing 100 ng/mL VEGF and 100 U/mL heparin), Group 3 (injection with 4 μM K20E dissolved in 500 μL cold-Matrigel containing 100 ng/mL VEGF and 100 U/mL heparin), and Group 4 (injection with 8 μM K20E dissolved in 500 μL cold-Matrigel containing 100 ng/mL VEGF and 100 U/mL heparin). After 1 week adaptation, the mice were anesthetized and injected subcutaneously with pre-prepared cold-Matrigel gel mentioned above into the left groin region to form jelly-like plug under normal body temperature. The vascular endothelial cells will be attracted by Matrigel plug-released VEGF to form the new vessel within the Matrigel plug, whose process will be suppressed by anti-angiogenic substances added in the Matrigel plugs. After 7 days, the mice were sacrificed and the Matrigel plug was recovered and photographed. The harvested Matrigel plugs were further homogenized in 1× phosphate buffered saline (PBS) and then centrifuged at 10000×g for 10 min at 4° C. The Drabkin's Reagent (#D5941; Sigma-Aldrich, Louis, Mo., USA) was applied for examining the hemoglobin content in the supernatants of the homogenized Matrigel plugs according to the manufacturer's instructions. Hemoglobin contained in the red blood cells should be just exist in a vessel with well-function and structure, thus hemoglobin content could be considered as an index of vessel formation within the Matrigel plug.

Cell Cycle Analysis

The experiments were performed according to our previous report with minor modifications (Pan et al., 2010). Briefly, the HUVECs (5×105 cells/well) were seeded on 6-well plated and harvested after 24 h treatment of K20E (0.5, 1, and 2 µM). Harvested cells were fixed with 70% ice-cold ethanol overnight. Cell pellets were centrifuged (1500 rpm, 5 min, 4° C.) and then re-suspended in 500 µL of DNA staining buffer containing 4 µg/mL propidium iodide, 1% Triton X-100, and 0.5 mg/mL of RNase A. After incubation at 37° C. (water bath) for 30 min in the dark, the cell cycle phase distributions were detected and analyzed by using FACSCanto flow cytometer (BD Biosciences, San Jose, Calif., USA) and ModFit LT Program (Verify Software House, Topsham, Me., USA), respectively.

Cell Migration and Invasion Assay

For evaluating cell migration, the HUVECs (1×105 cells/well) suspended within serum-free culture medium were seeded on inner surface of the upper chamber (ThinCerts™ Cell Culture Inserts with 8 µm pore size; #662638; Greiner Bio-One Inc., Monroe, N.C., USA) placed in the lower chamber (wells of a 24-well plate). For examining the cell invasion, the HUVECs were pre-mixed with equal volume of thawed Matrigel and rapidly seeded on the upper chamber. After 2 h for cell attachment, K20E at different concentrations (0.5, 1, and 2 µM) were added in the upper and the lower chambers, while 5% FBS as a chemoattractant was added in the lower chamber to facilitate cell migration or invasion. After 16 h incubation, the culture medium (or Matrigel) was removed clearly from inside the upper chamber, and the migrated or invasion cells attached on the outer surface of the upper chamber were fixed with 10% formaldehyde for 10 min at RT. The fixed cells were subsequently counterstained with hematoxylin. Relative cell number of each groups was counted from five random regions by light microscopy using a 40-fold magnification. The cell number of the control group (treated with 5% FBS alone) was defined as 100%.

Tube Formation Analysis

The experiments were performed as described previously (Pan et al., 2010). The HUVECs (lx 104 cells/well) were seeded on Matrigel-coated wells of a 96-well plate and then incubated with various concentrations (0.5, 1, and 2 µM) of K20E for 8 h. After that, the capillary-like tube formation was observed by light microscopy at 40-fold magnification, and the tube lengths of the capillary mesh were measured to evaluate anti-angiogenic effect of K20E. The tube length of the control group (treated with 5% FBS alone) was defined as 100%.

Western Blot

The experiments were carried out as described previously (Pan et al., 2010). Briefly, the cells (5×105 cells/well) seeded on the 6-well plates and incubated with different concentrations (0.5, 1, and 2 µM) of K20E under normal culture condition for 15 min or 24 h to detect the expression levels of the phosphorylated proteins and the total proteins, respectively. The treated cells were harvested and lysed by using PROPREP® protein extraction solution (#17081; iNtRON Biotechnology, Gyeonggi-Do, South Korea). The cell lysates were further centrifuged at 13000×g at 4° C. for 10 min to collect the supernatants for sodium dodecyl sulfate-polyacrylamide gel electrophoresis (SDS-PAGE). Protein concentration was measured by the Bio-Rad protein assay kit (Bio-Rad, Hercules, Calif., USA) according to the manufacturer's instructions. Aliquots containing 30 µg protein were electrophoresed using 10% slab SDS-PAGE gels and then transferred to PVDF membranes (Immobilon-P™; Millipore, Bedford, Mass., USA). After blocking nonspecific binding sites by 5% (w/v) non-fat milk at RT for 1 h, the membrane was were incubated with primary antibodies (1:1,000 dilution), followed by horseradish peroxidase-conjugated secondary antibodies (1:2,000 dilution). Substrates were visualized by using Amersham ECL Plus™ Western Blotting Detection Reagents (GE Healthcare Bio-Sciences, Bucks, UK). The luminescence signal was acquired by Fujifilm LAS-4000 system (San Leandro, Calif., USA) and quantified by using MultiGauge software (v3.0; Fujifilm). The results for each experiment were normalized to the band density of β-actin. The relative protein expression was calculated according to the values of the control group (treated with 5% or 10% FBS alone) as 100%.

Quantification of VEGF Level in Culture Medium

The LLC1 cancer cells (5×105 cells/well) were seeded on the 6-well plate and then incubated with various concentrations (0.5, 1, 2, and 4 µM) of K20E in total volume of 1 mL culture medium for 24 h. After that, the culture medium was harvested to measure the VEGF level by ELISA kit (#SEA143Mu) according to the manufacturer's instructions (Bio-Connect Diagnostics, Huissen, Netherlands).

Gelatin Zymography

The experiments were carried out according to the procedure of previous study with minor modification (Chen et al., 2012). Briefly, the cells (5×105 cells/well) seeded on the 6-well plates and incubated for 24 h under normal culture condition with several concentrations (0.5, 1, and 2 µM) of K20E. After that, the culture medium was collected and centrifuged at 12000 rpm for 10 min at 4° C. The supernatants (32 µL) was mixed with 8 µL of 5× non-reducing loading buffer (12.5% bromophenol blue, 10% SDS, 0.5 M Tris-HCl pH=6.8, and 50% glycerol) and then resolved in 8% slab SDS-PAGE gels with 0.1% gelatin. After electrophoresis, the gels were washed by 2.5% Triton X-100 for 10 min thrice and then incubated with the developing buffer (0.01% NaN3, 10 mM CaCl2, and 40 mM Tris-HCl pH=8.0) for an additional 24 h at 37° C. After that, the gels were stained with the staining solution (0.125% coomassie blue R-250, 50% methanol, and 10% acetic acid) for 1 h at RT and then destained with the destaining buffer (40% methanol and 10% acetic acid) until the gelatinase-digested bands are visible. The intensity of the digested bands was quantified by using Multi Gauge software. The relative gelatinase activity was calculated according to the values of the control group (treated with 5% FBS alone) as 100%.

Data Analysis

All data are presented as mean±standard deviation (S.D.). The experiments were done in triplicate. Statistical significance was evaluated by one-way ANOVA. A value of P b 0.05 was regarded as being statistically significant.

Preparation Examples

Example 1 Synthesis and Identification of K20

The solution of isoeugenol (10 g in 100 mL dichloromethane) was added in drop to the solution of iodobenzene diacetate (IDA; 10 g) in 100 mL of dichloromethane (dry with CaH2) under room temperature (RT) for 4 h. After 48 h, NaHCO3 (3 g) was added to the solution and stirred for 1 h. The mixture was filtrated and the filtrate was evaporated under reduced pressure to give the intermediate 1. The intermediate 1 (1.12 g) and dichlorodicyano-benzoquinone (DDQ; 3.24 g) were resolved in 50 mL of 1,4-dioxane. The solution was then refluxed. After 48 h, the solution was filtrated and the filtrate was evaporated under reduced pressure to give the intermediate 2. The solution of the intermediate 2 (1.33 g in 20 mL of CH3OH) with 10% PtO2 (96.3 mg in H2O) was stirred under H2 at RT. After 6 h, the mixture was filtrated and the filtrate was evaporated under reduced pressure to give the intermediate 3. The solution of the intermediate 3 (0.64 g in 20 mL ethanol) with SeO2 (0.42 g) was refluxed. After 12 h, the mixture was evaporated under reduced pressure and then adds 30 mL of ethyl acetate (EtOAc). The mixture was filtrated by celite and the filtrate was evaporated under reduced pressure. And then the residue was purified by silica gel column chromatography (Silica gel 60, Merck 70-230 mesh) eluting with EtOAc/hexane (1:5) to give compound K20. 1H-NMR (CDCl3) δH 10.25 (s, 1H, CHO), 7.64 (s, 1H, H-2'), 7.37 (d, J=8.0 Hz, 1H, H-6'), 7.35 (s, 1H, H-4), 7.04 (d, J=8.0 Hz, 1H, H-5'), 6.73 (s, 1H, H-6), 6.11 (br s, 1H, Ph-OH), 4.00 (s, 3H, OMe), 3.97 (s, 3H, OMe), 3.69 (t, J=6.5 Hz, 2H, H-3"), 2.80 (t, J=7.3 Hz, 2H, H-1"), 1.94 (m, 2H, H-2"); 13C-NMR (CDCl3) δC 186.8, 165.9, 148.7, 146.9, 144.6, 141.6, 139.9, 127.3, 123.7, 120.6, 116.7, 115.0, 113.5, 111.0, 108.8, 62.2, 56.3, 56.1, 34.7, 32.5; IR (KBr) vmax: 3513, 3435, 2940, 2864, 1637, 1601, 1522, 1490, 1409, 1273, 1139, 1061, 818 cm-1; ELMS m/z (%) (70 eV) 356 (M+, 60; C20H20O6), 312 (100), 269 (7), 197 (6), 152 (6), 137 (6), 126 (4), 105 (4), 91 (4), 55 (4).

Example 2 Synthesis and Identification of K20A

Didehydroisoeugenol (1.15 g) and DDQ (0.870 g) were dissolved in the 10 mL of mixture of CH2Cl/H2O (4:1) and stirred for 48 hr. After filtration, the filtrate was purified by silica gel column chromatography to give compound K20A. 1H-NMR (CDCl3) δH 9.64 (d, J=7.6 Hz, 1H, H-3"), 7.41 (d, J=15.8 Hz, 1H, H-1"), 7.02 (s, 1H, H-4), 6.99 (s, 1H, H-6), 6.97 (d, J=8.1 Hz, 2H, H-6'), 6.89 (s, 1H, H-2'), 6.87 (1d, J=8.1 Hz, 1H, H-5'), 6.60 (dd, J=15.8, 7.6 Hz, H-2"), 5.66 (s, 1H, ph-OH), 5.18 (d, J=9.2 Hz, 1H, H-2), 3.50 (m, 1H, H-3), 1.40 (d, J=6.8 Hz, 3H, C-3-Me); 13C-NMR (CDCl3) δC 193.6, 153.2, 150.6, 146.7, 146.0, 144.6, 134.0, 131.2, 128.1, 126.3, 119.9, 117.3, 114.3, 111.8, 108.9, 94.5, 56.0, 55.9, 45.1, 17.7; IR (KBr) vmax: 3486, 2985, 2852, 2851, 2734, 1684, 1620, 1478, 1133, 821 cm-1; MS (70 eV; EI) m/z (%): 340 (M+, 100; C20H20O5), 325 (7), 137 (15), 97 (15), 71 (18), 57 (30).

Example 3 Synthesis and Identification of K20E

Methyl caffeate (762 mg) was dissolved in a mixture of 20 mL of benzene and 30 mL of acetone. After that, silver oxide (1.82 g) was added into above reaction mixture and further stirred under RT for 60 h. The filtrate of the mixture was purified to yield an intermediate compound (341 mg) by silica gel column chromatography (Silica gel 60, Merck 70-230 mesh) eluting with EtOAc/heptane (1:1) (Pieters et al., 1999). The intermediate was further acetylated to generate the final product, K20E, which was purified by silica gel column chromatography eluting with ethyl acetate/heptane (1:1). The molecular formula of K20E compound was established as C26H24O11 ([M+H]+m/z 513.4708); 1H-NMR (CDCl3 300 MHz) δ: 2.27 (6H, s, OAc), 2.30 (3H, s, OAc), 3.78 (3H, s, OMe), 3.83 (3H, s, OMe), 4.28 (1H, d, J=7.4 Hz, H-3), 6.19 (1H, d, J=7.4 Hz, H-2), 6.29 (1H, d, J=15.8 Hz, H-2"), 7.17 (1H, d, J=8.4 Hz, H-5'), 7.19 (1H, s, H-6), 7.21 (1H, d, J=1.9 Hz, H-2'), 7.28 (1H, dd, J=8.4, 1.9 Hz, H-6'), 7.42 (1H, s, H-4), 7.59 (1H, d, J=15.8 Hz, H-1"); IR (KBr) vmax: 3074, 3016, 1776 (Ar—OCOCH3), 1739, 1716 (—COOMe), 1643 ( ), 1612, 1492 (aromatic), 1273, 1203 and 1176 cm-1.

Example 4 Synthesis and Identification of K20B

K20E (2.12 g) and DDQ (3.24 g) were resolved in 50 mL of 1,4-dioxane. The solution was then refluxed. After 48 h, the solution was filtrated and the filtrate was evaporated under reduced pressure. And then the residue was purified by silica gel column chromatography to give compound K20B. 1H-NMR (CDCl3 300 MHz) δ: 2.31 (3H, s, OAc), 2.32 (3H, s, OAc), 2.42 (3H, s, OAc), 3.80 (3H, s, COOMe), 3.95 (3H, s, COOMe), 6.44 (1H, d, J=16.1 Hz, H-2"), 7.30~7.33 (2H, m, H-2', H-5'), 7.77 (1H, d, J=16.1 Hz, H-1"), 7.88~7.92 (2H, m, H-6, H-6'), 8.06 (1H, d, J=1.3 Hz, H-4); 13C-NMR (CDCl3 75 MHz) δ: 20.6, 20.7, 51.7, 52.0, 109.8, 117.7, 118.2, 121.0, 123.3, 125.0, 127.2, 128.0, 131.7, 135.3, 141.7, 144.0, 144.1, 145.9, 160.0, 163.4, 167.2, 167.8, 168.0, 168.1; IR (KBr) vmax: 3006, 2957, 2848, 1779, 1717, 1642, 1616, 1501, 1438, 1378, 1213, 1084, 1022, 899, 863 cm-1; MS (70 eV, EI) m/z (%): 510 (M+, 8), 468 (20), 426 (34), 414 (23), 384 (100), 352 (35), 322 (30), 178 (15), 97 (21), 83 (25), 69 (35), 58 (43).

Example 5 Synthesis and Identification of K20L

The solution of methyl ferulate (10 g; in 10 mL of acetone) was added in drop to the solution of IDA (10 g) in 100 mL of dichloromethane (dry with CaH$_2$) under RT for 4 h. After 48 h, NaHCO3 (3 g) was added to the solution and stirred for 1 h. The mixture was filtrated and the filtrate was evaporated under reduced pressure to give compound K20L. And then the residue was purified by silica gel column chromatography eluting with EtOAc/hexane (1:9) to give compound K20L. 1H-NMR (CDCl3) δH: 7.64 (d, J=15.9 Hz, 1H, H-1"), 7.17 (s, 1H, H-4), 7.00 (s, 1H, H-6), 6.88 (s, 3H, H-2', H-5', H-6'), 6.30 (d, J=15.9 Hz, 1H, H-2"), 6.09 (d, J=8.1 Hz, 1H, H-2), 5.63 (s, 1H, Ph-OH), 4.33 (d, J=8.1 Hz, 1H, H-3), 3.89 (s, 3H, OMe), 3.86 (s, 3H, OMe), 3.81 (s, 3H, COOMe), 3.79 (s, 3H, COOMe); 13C-NMR (CDCl3) δC: 170.7, 167.6, 146.0, 144.7, 144.6, 131.3, 128.5, 125.6, 119.4, 117.8, 115.5, 114.5, 112.0, 108.7, 87.4, 56.0, 55.9, 55.4, 52.8, 51.6; IR (KBr) vmax: 3396, 3011, 2956, 2849, 1741, 1637, 1606, 1496, 1440, 1287, 837, 612 cm-1; MS (70 eV, EI) m/z (%): 414 (M+, 95; C22H22O8), 382 (100), 350 (73), 280 (15), 266 (12), 167 (8), 151 (7), 137 (6), 58 (18).

Biological Assessment

Example 6 K20E Possessed Antitumor and Anti-Angiogenic Effects

Methyl caffeate and K20 series compounds were tested to determine their inhibitory effects on cell growth of HUVECs by MTT assay. The experimental data suggested that K20E exhibited the highest potency in suppressing cell growth of HUVECs among all tested compounds (see the Table below). Thereby, K20E was subjected to explore its pharmacological mechanisms in subsequent experiments.

| Compounds | GI$_{50}$ (HUVECs) |
|---|---|
| Methyl caffeate | 80 µM |
| K20 | 61 µM |
| K20A | 24 µM |
| K20B | 24 µM |
| K20E | 7.5 µM |
| K20L | 32 µM |

The mouse allograft lung tumor model was applied to evaluate the in vivo antitumor activity of K20E in the present study. Our result showed that the tumor mass was dose-dependently reduced in the LLC1-bearing tumor mice after 2-week K20E treatment (FIG. 1A). The tumor mass was significantly reduced by 8 mg/kg/day of K20 as compared to the control group (P b 0.05).

Figure 1B:
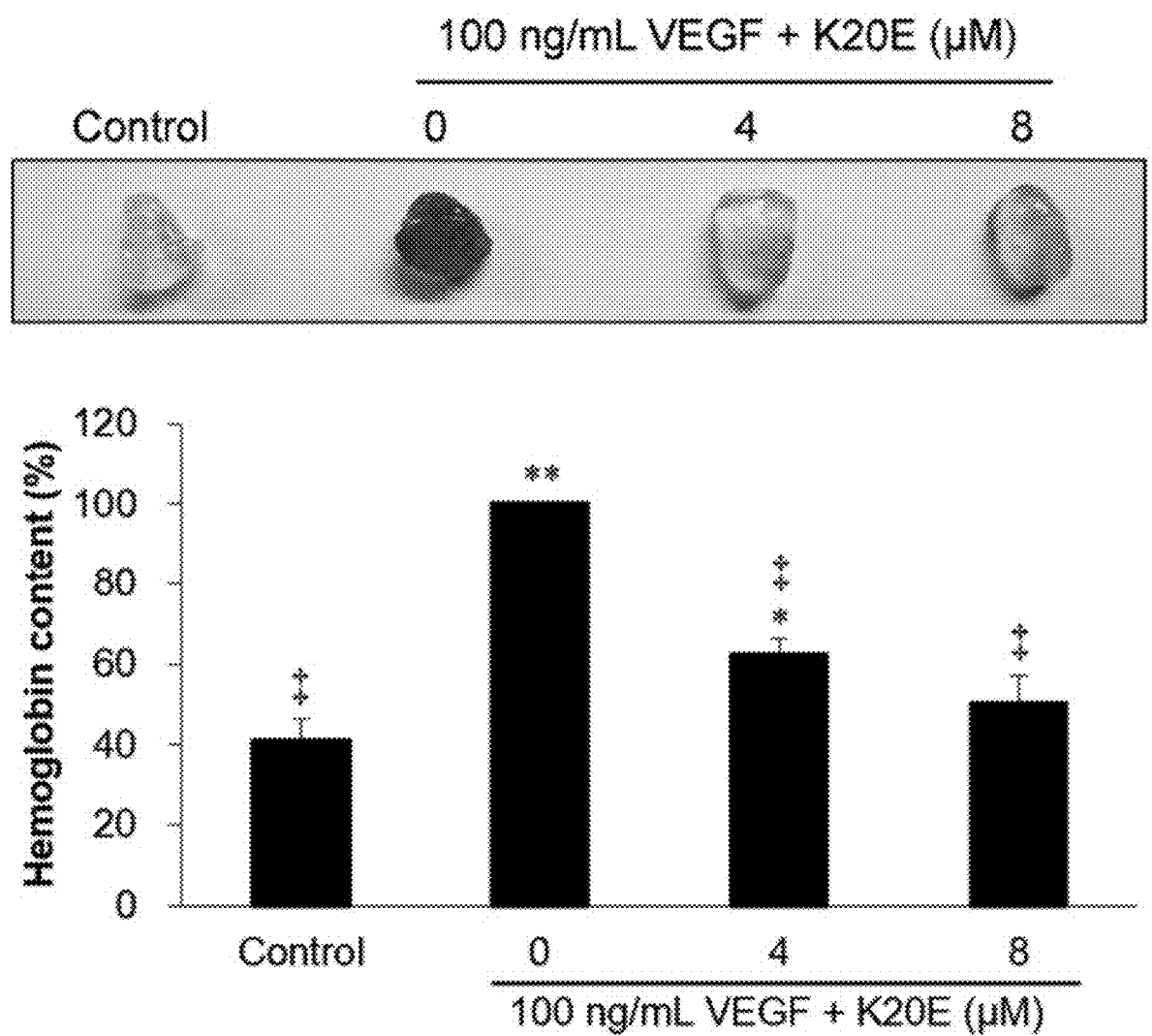

To further elucidate the effect of K20E on anti-angiogenesis, Matrigel mixed with VEGF was implanted subcutaneously in mice to evaluate the anti-neovascularization effects of K20E (FIG. 1B). Our study showed that neovessel formation (shown as red color) was markedly stimulated within the Matrigel plug with VEGF as compared with the control group (without VEGF supplement), which was significantly decreased by higher dose (4 and 8 µM) of K20E in a dose-dependent manner (FIG. 1B; upper panel) rather than lower dose (1 and 2 µM). Similarly, quantification of the hemoglobin content of the harvested plugs supported the above observations (lower panel; FIG. 1B). Experimental data revealed that K20E treatment obviously diminished the hemoglobin content of the implanted Matrigel plugs with VEGF in a dose-dependent manner as compared to the Matrigel with VEGF alone. The ex vivo supplementary data, the chick chorioallantoic membrane (CAM) assay, also supported that K20E can effectively reduce the angiogenesis in a dose-dependent manner.

Example 7 K20E Exhibited the Growth Inhibition in the LLC1 Cells and the HUVECs

Figure 2A:
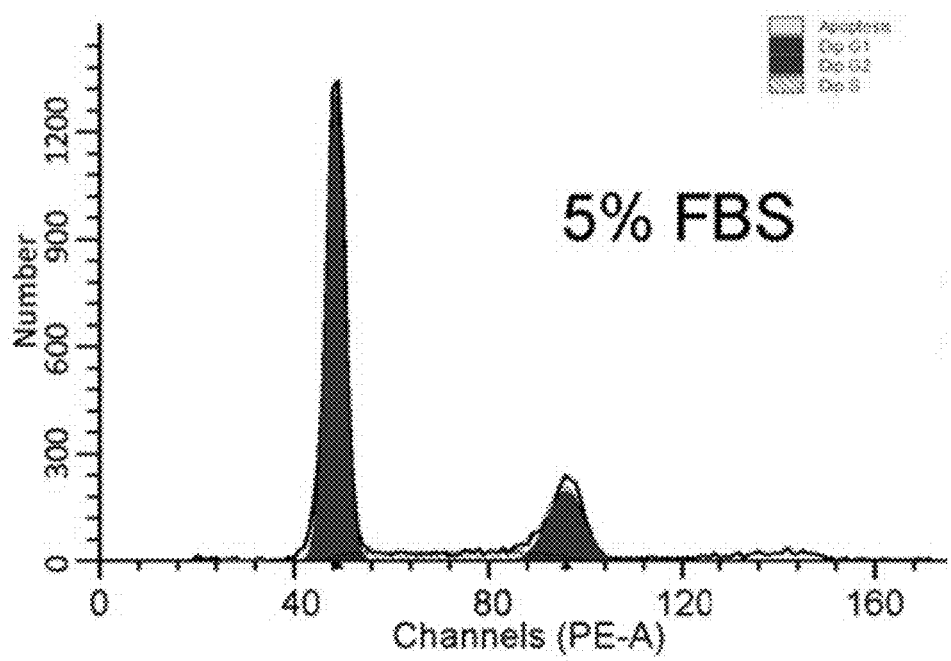
FIGS. 2A-E show growth inhibition of K20E. The cells treated with several concentrations of K20E to analyze cell cycle by using flowcytometry. *P<0.05 and **P<0.01 compared to the control group (treated with 5% FBS alone), respectively. 5% FBS-stimulated cell growth of the HUVECs can be markedly reduced by K20E treatment in a dose-dependent manner (FIG. 2A). The cell cycle distributions were analyzed in the cells treated with K20E at different concentrations (0.5, 1, and 2 μM; see FIGS. 2B, C and D) and the results suggested that 0.5 and 1 μM of K20E can significantly induce cells in sub-G1 phases (apoptosis) and arrest cells in G2/M phase in the HUVECs, respectively (FIG. 2E).

To differentiate the inhibitory effects of K20E between cancer cells and vascular endothelial cells (VECs), the growth inhibition of K20E was individually verified in both cells. Our data showed that K20E can significantly inhibit the cell viability of the LLC1 lung cancer cells under normal culture condition. The GI50 value, the concentration that causes 50% growth inhibition, of K20E on LLC1 is about 79.4 µM (data not shown). Similarly, 5% FBS-stimulated cell growth of the HUVECs can be markedly reduced by K20E treatment in a dose-dependent manner (FIG. 2A). The GI50 value of K20E on HUVECs is about 7.5 µM (see the above table). These data suggested that K20E to be more effective in antiangiogenesis than anti-cancer according to the GI50 values. Accordingly, the pharmacological mechanisms of K20E were focused on antiangiogenesis in the following experiments. Moreover, to reduce the non-specific cytotoxicity of K20E, low concentrations (0.5, 1, and 2 µM; approximately equal to GI10 value) of K20E were used in following studies.

Figure 2B:
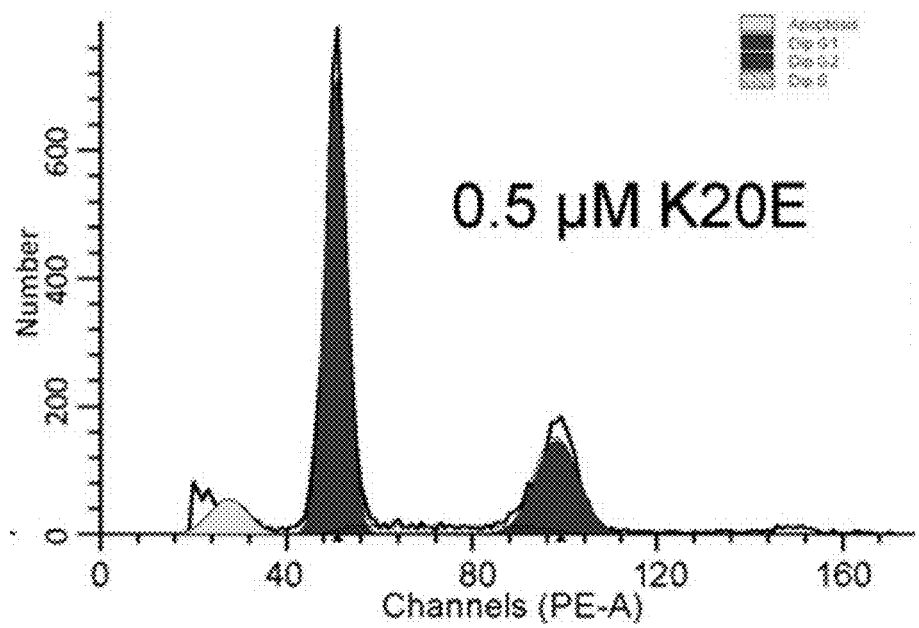
Figure 2C:
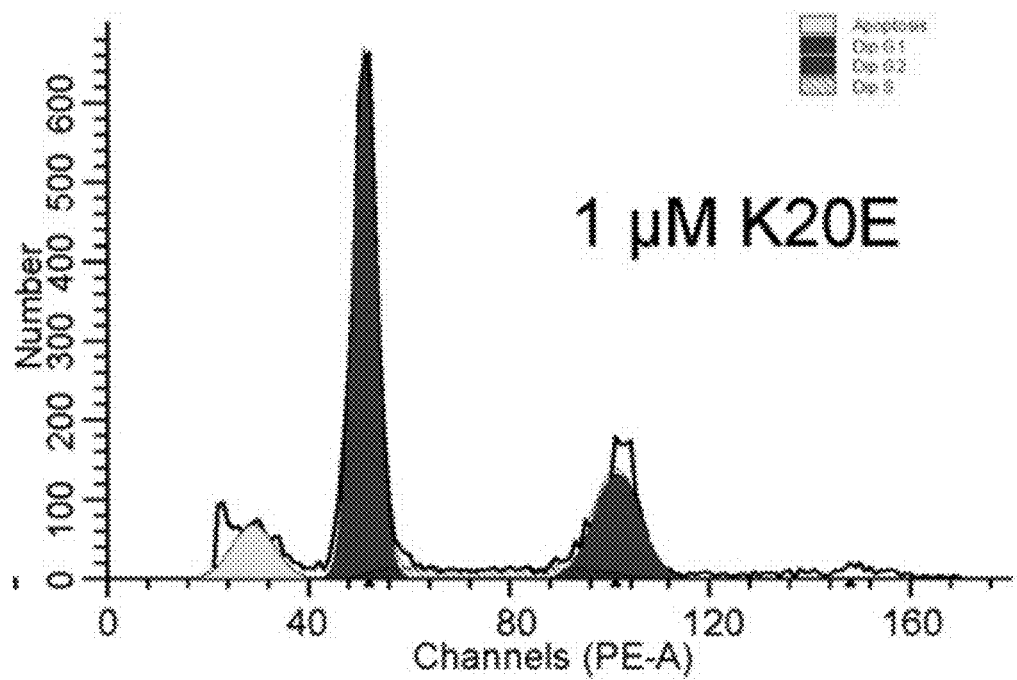
Figure 2D:
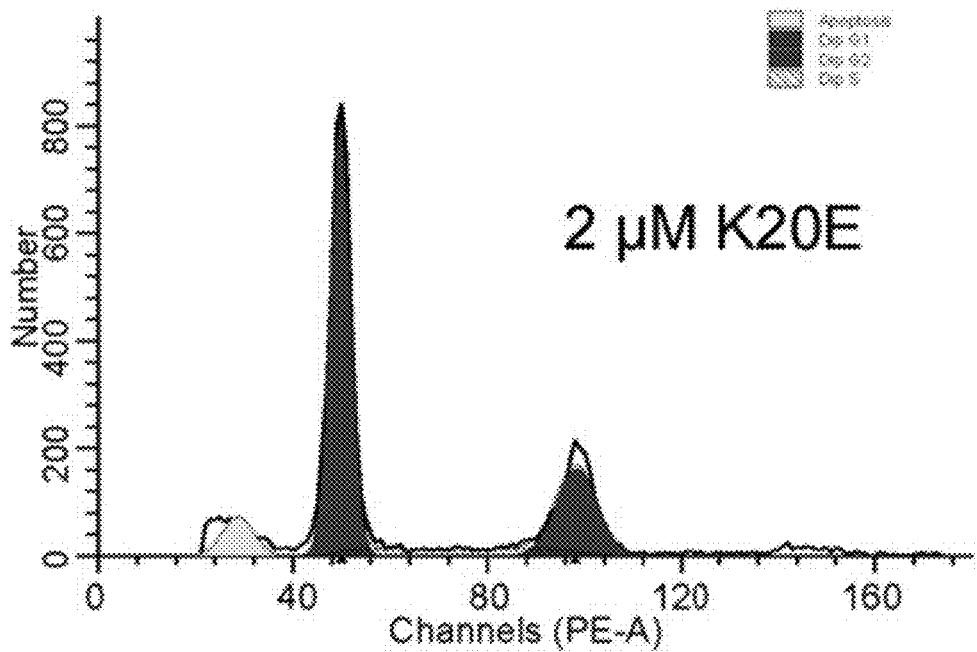
Figure 2E:
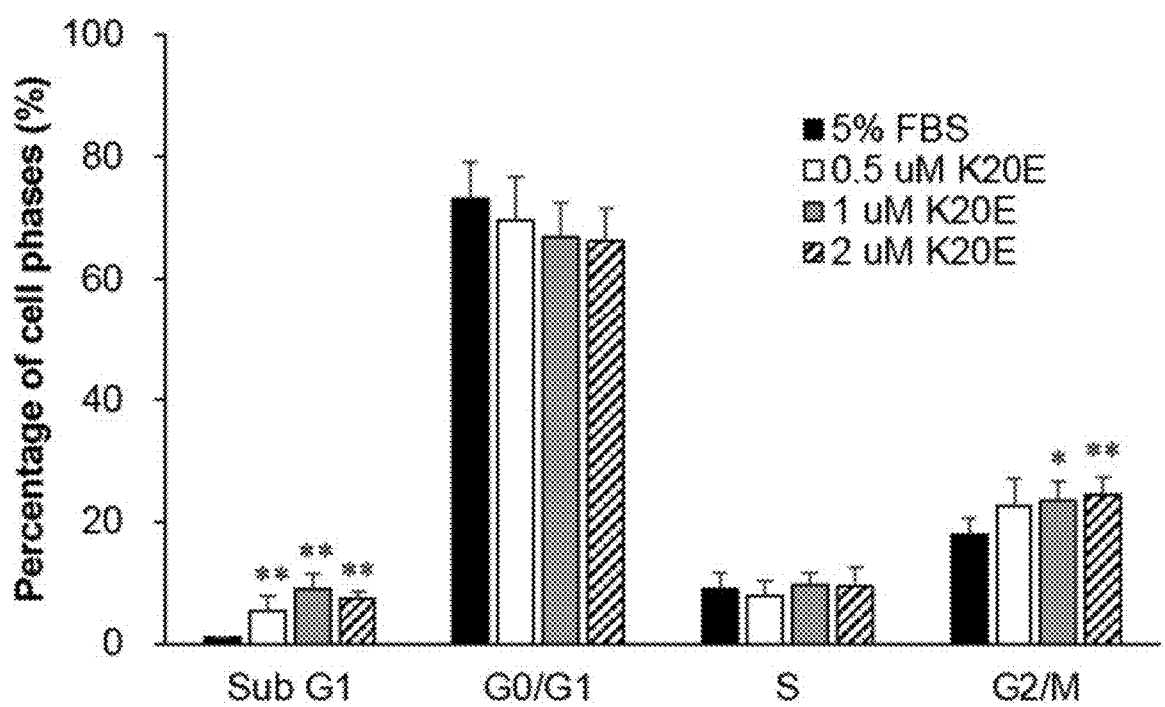

To further determine the growth inhibition of K20E on HUVECs, the cell cycle distributions were analyzed in the cells treated with K20E at different concentrations (0.5, 1, and 2 µM; see FIGS. 2B, C and D). The results suggested that 0.5 and 1 µM of K20E can significantly induce cells in sub-G1 phases (apoptosis) and arrest cells in G2/M phase in the HUVECs, respectively (FIG. 2E).

Example 8 K20E Reduced the HUVEC Migration and Invasion

Figure 3A:
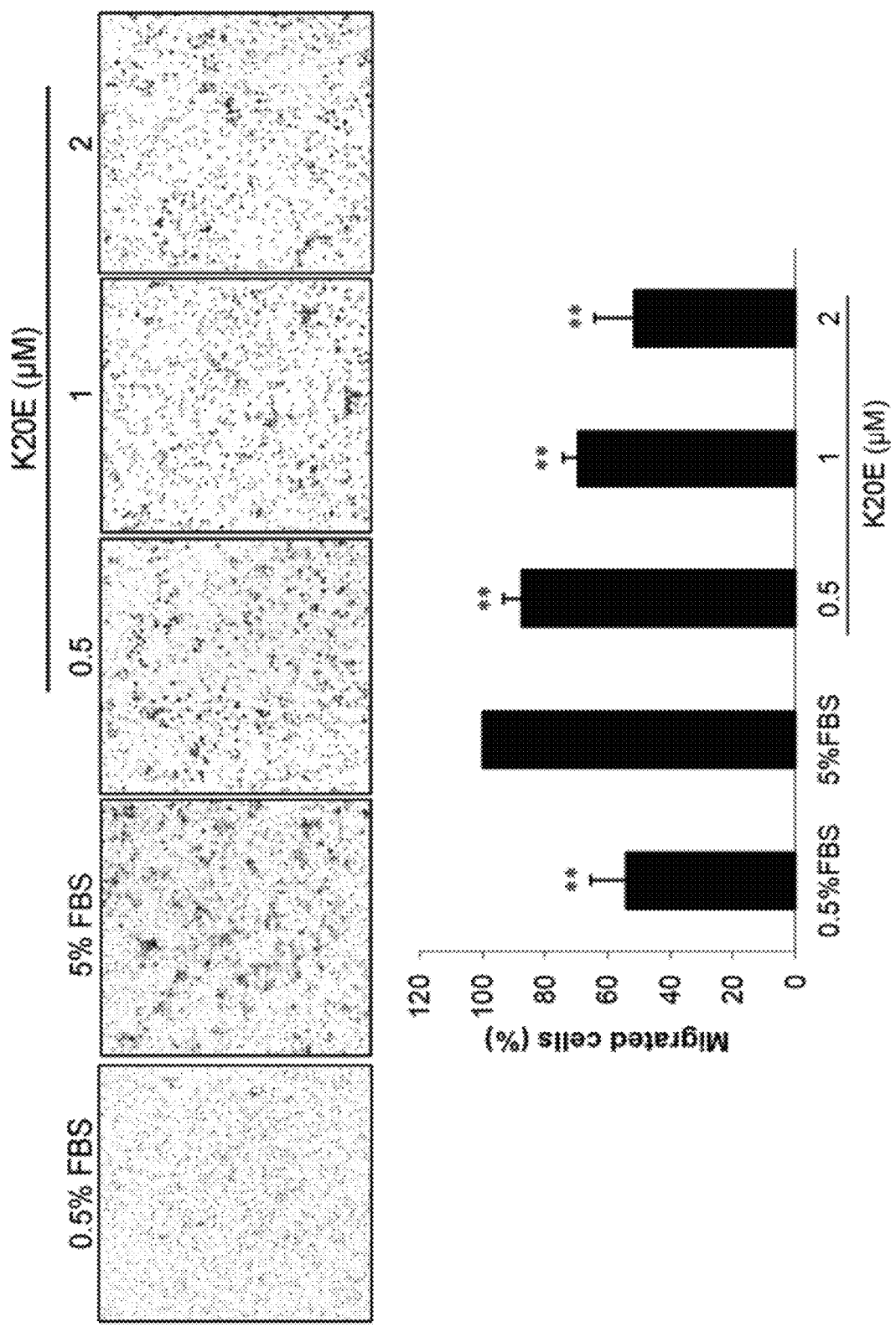
FIGS. 3A-B show suppressions of K20E on the HUVEC migration and invasion. The cell migration and invasion of the HUVECs treated with K20E were examined by using Transwell migration assay (FIG. 3A) and Matrigel invasion assay (FIG. 3B), respectively. The images were captured under the microscopy at 40-fold magnification (upper panel), and the statistical results of the captured images were showed as the bar chat (lower panel). **P<0.01 compared to the control group (treated with 5% FBS alone).
Figure 3B:
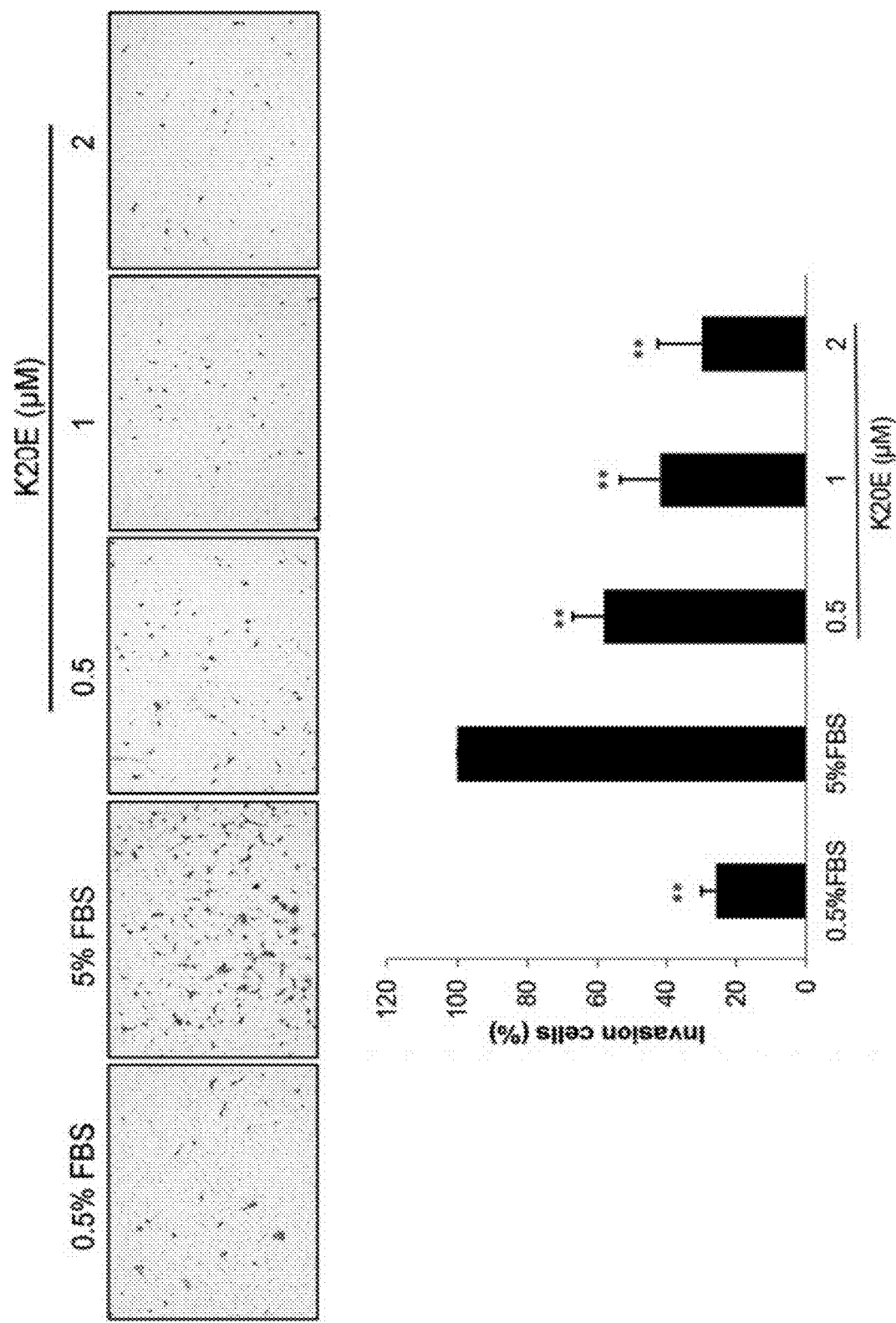

Cell motility (migration and invasion) of the VECs is the initial event in the formation of the new peritumoral blood vessels. Our results indicated that migration of the HUVECs can be significantly increased by 5% FBS, whose effect can be markedly abolished by 0.5 µM of K20E (FIG. 3A). Likewise, 5% FBS stimulation also markedly facilitated the cell invasion of the HUVECs, whose activity can be largely suppressed in the cells treated with 0.5 µM of K20E (FIG. 3B).

Example 9 K20E Decreased the Formation of Tubular-Like Network of HUVECs

Figure 4:
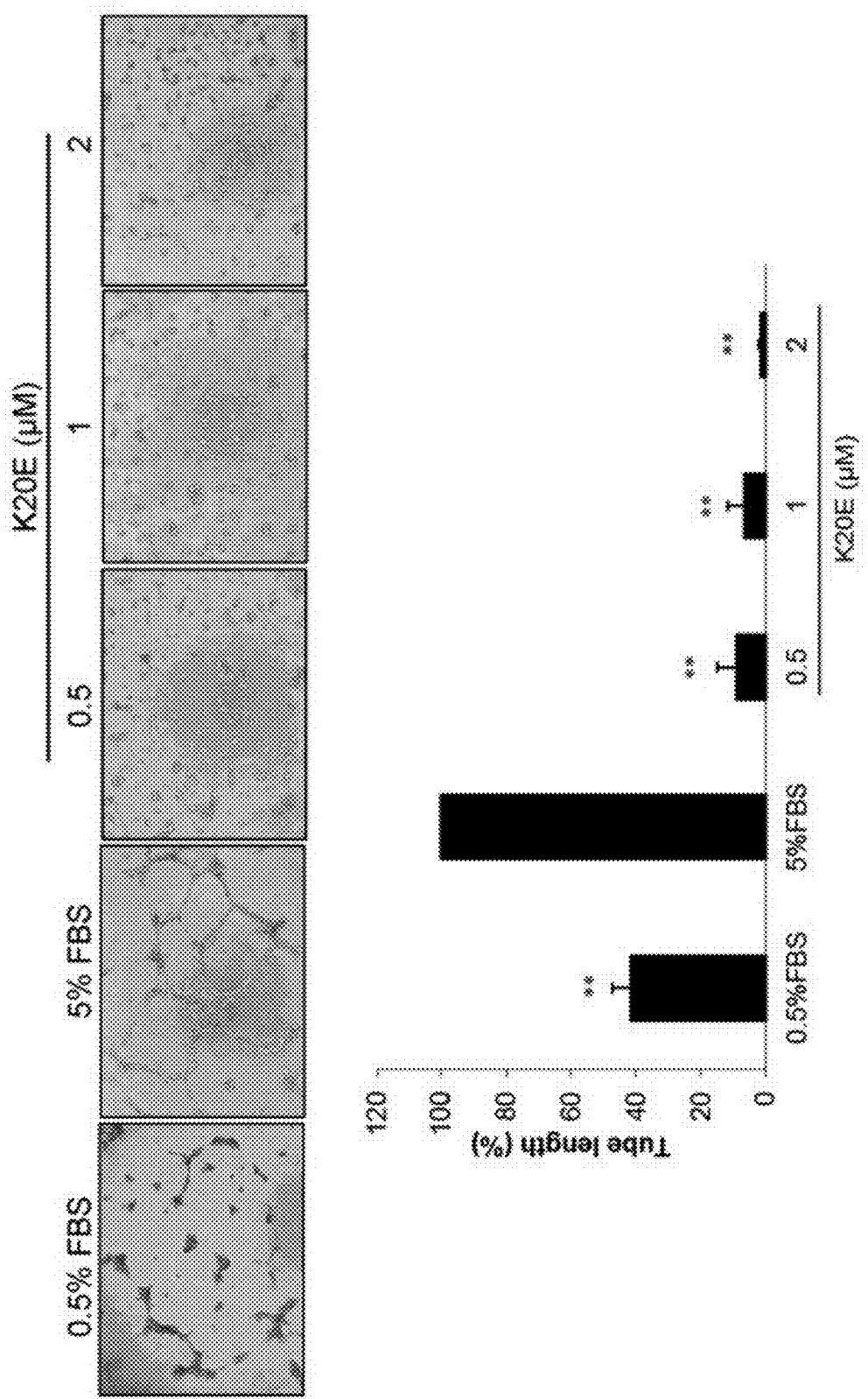
FIG. 4 shows regulation of K20E on the formation of tubular-like network of the HUVECs. The images were captured under the microscopy at 40-fold magnification (upper panel), and the statistical results of the captured images were presented as the bar chat (lower panel). **P<0.01 compared to the control group (treated with 5% FBS alone).

Formation of the tubular-like network, an important step in the angiogenic process, can be found in the HUVECs grown on extracellular matrix (ECM) with angiogenesis-promoting stimulators. Our study revealed that the tube formation of the HUVECs on Matrigel can be induced after 8 h treatment with 5% FBS (as the angiogenic stimulator), whose induction can be significantly suppressed by K20E treatment in a dose-dependent manner (FIG. 4).

Figure 5A:
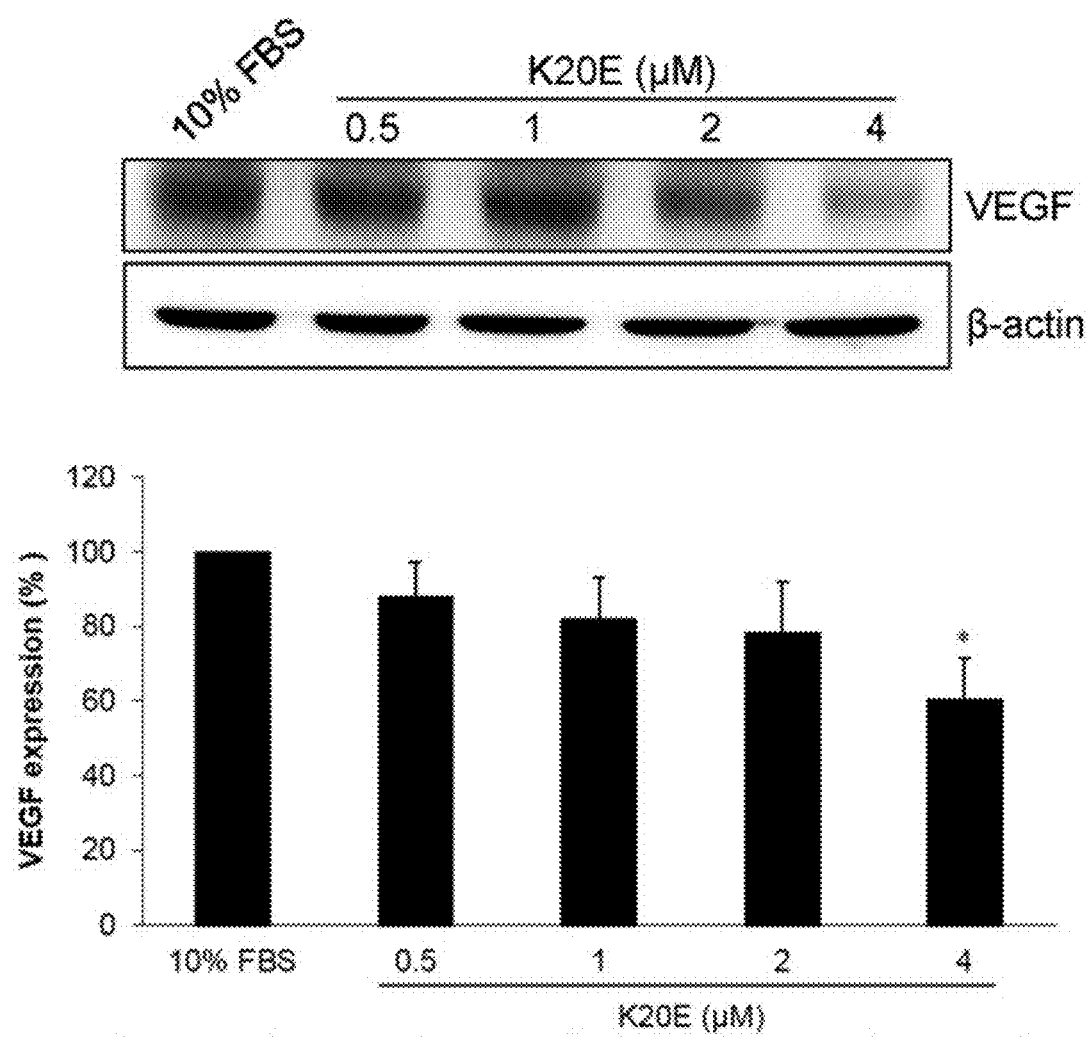
FIGS. 5A-B show inhibitory regulations of K20E on VEGF expression in the LLC1 cancer cells (FIG. 5A). The levels of intracellular VEGF and secreted VEGF proteins were detected by using immunoblot and ELISA assay, respectively. *P<0.05 compared to the control group (treated with 10% FBS alone) (FIG. 5B).
Figure 5B:
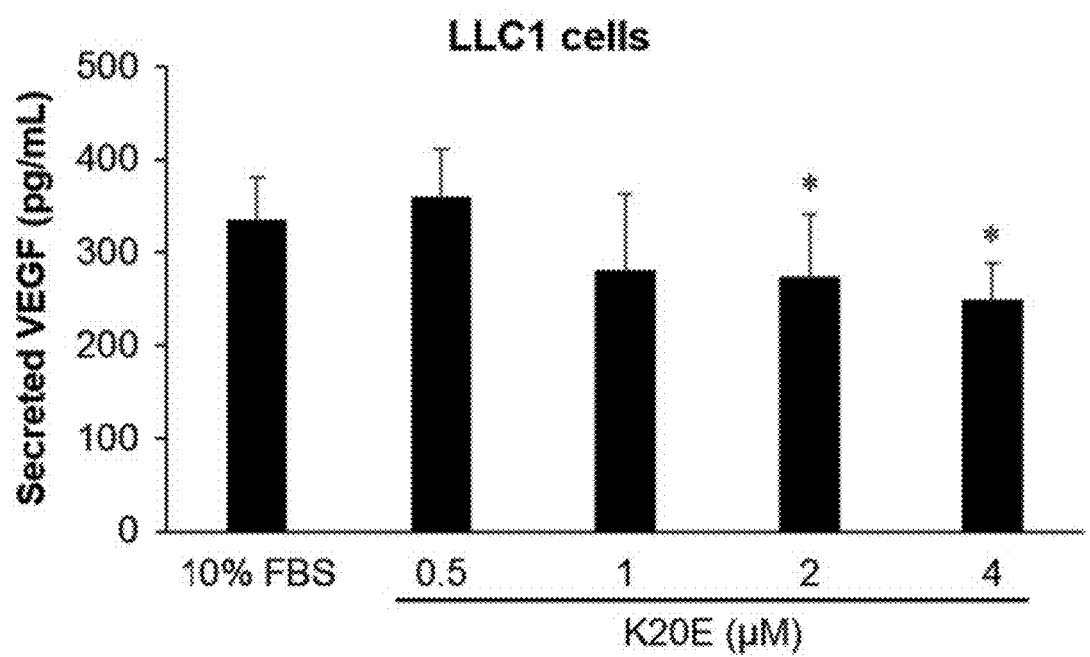
Figure 6A:
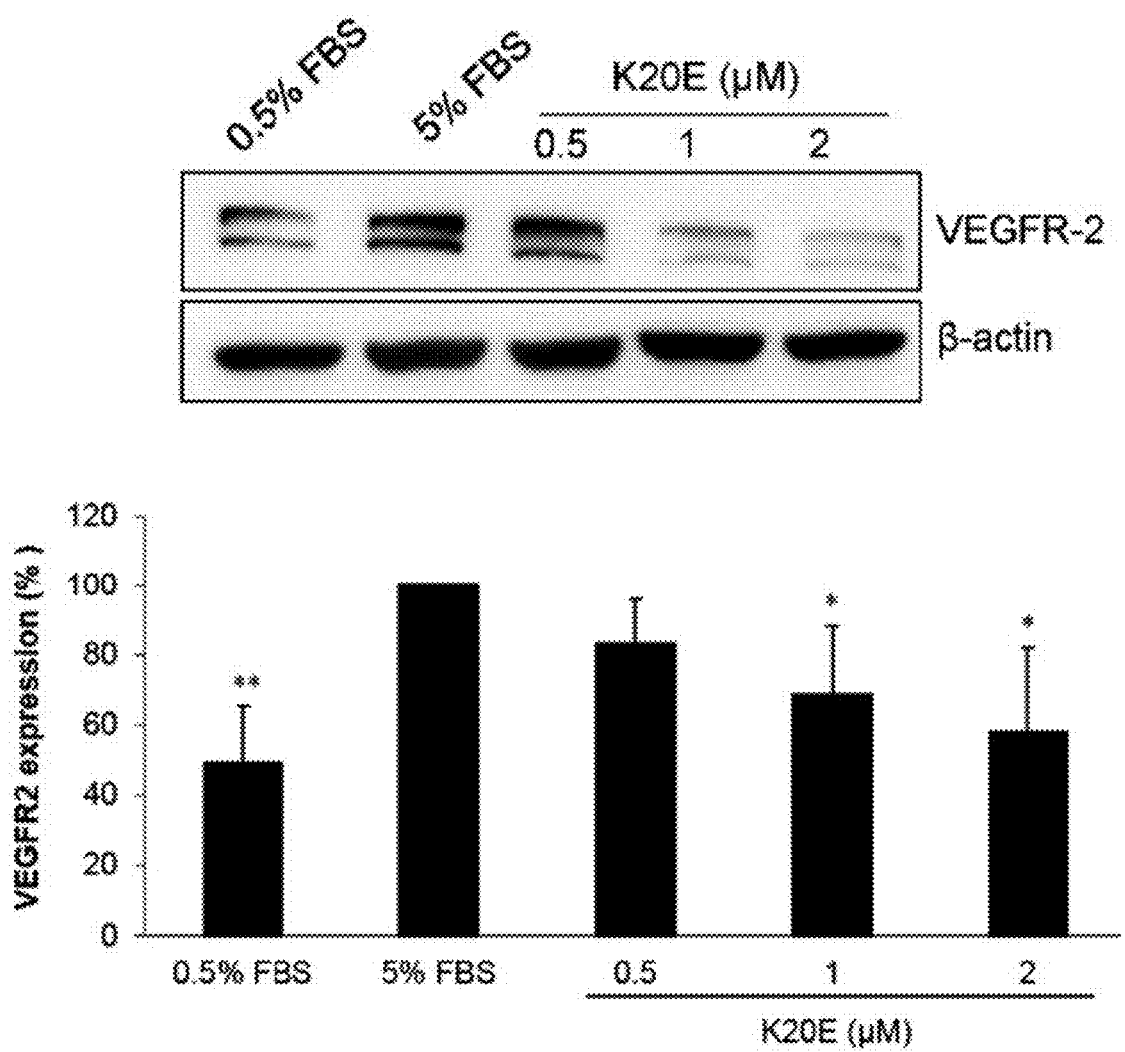
FIGS. 6A-D show inhibitory regulations of K20E on the protein levels of VEGFR-2, and VEGFR-2-mediated signaling cascades in the HUVEC cells. The expression levels of VEGFR-2 (FIG. 6A), ERK1/2-MAPK cascade (FIG. 6B), AKT-mTOR pathway (FIG. 6C), and gelatinases (FIG. 6D, left panel) were detected by using immunoblot. Gelatinase activities (FIG. 6D, right panel) were evaluated by using gelatin zymography. *P<0.05 and **P<0.01 compared to the control group (treated with 5% FBS alone), respectively.
Figure 6B:
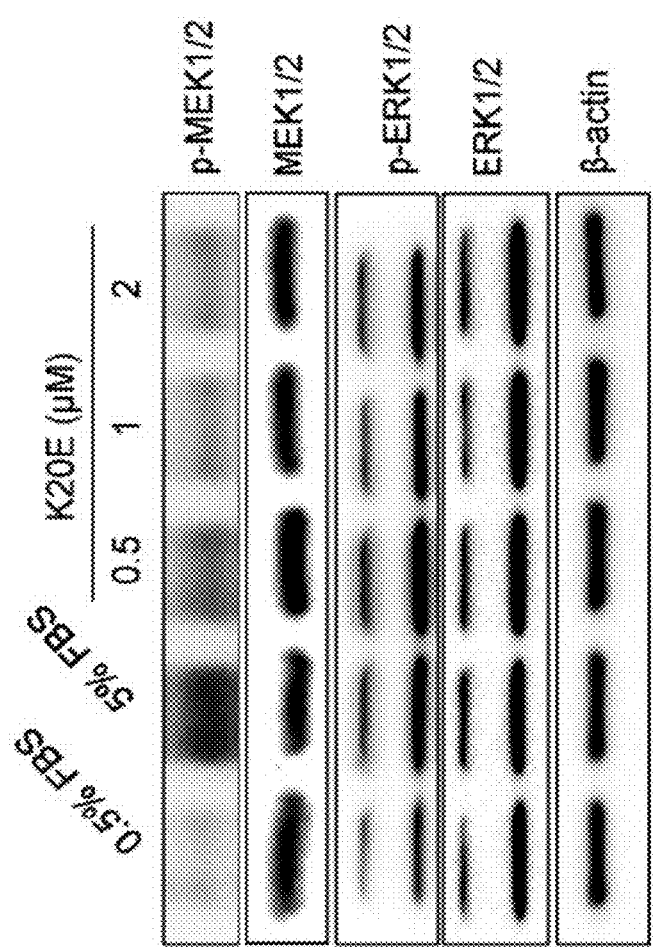
Figure 6B:
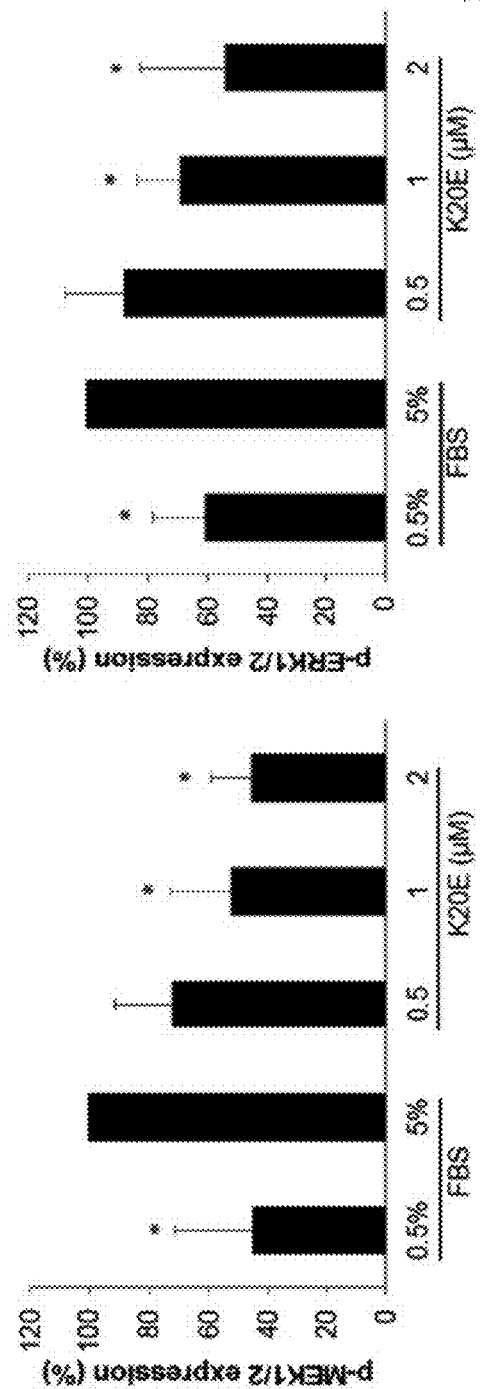
Figure 6C:
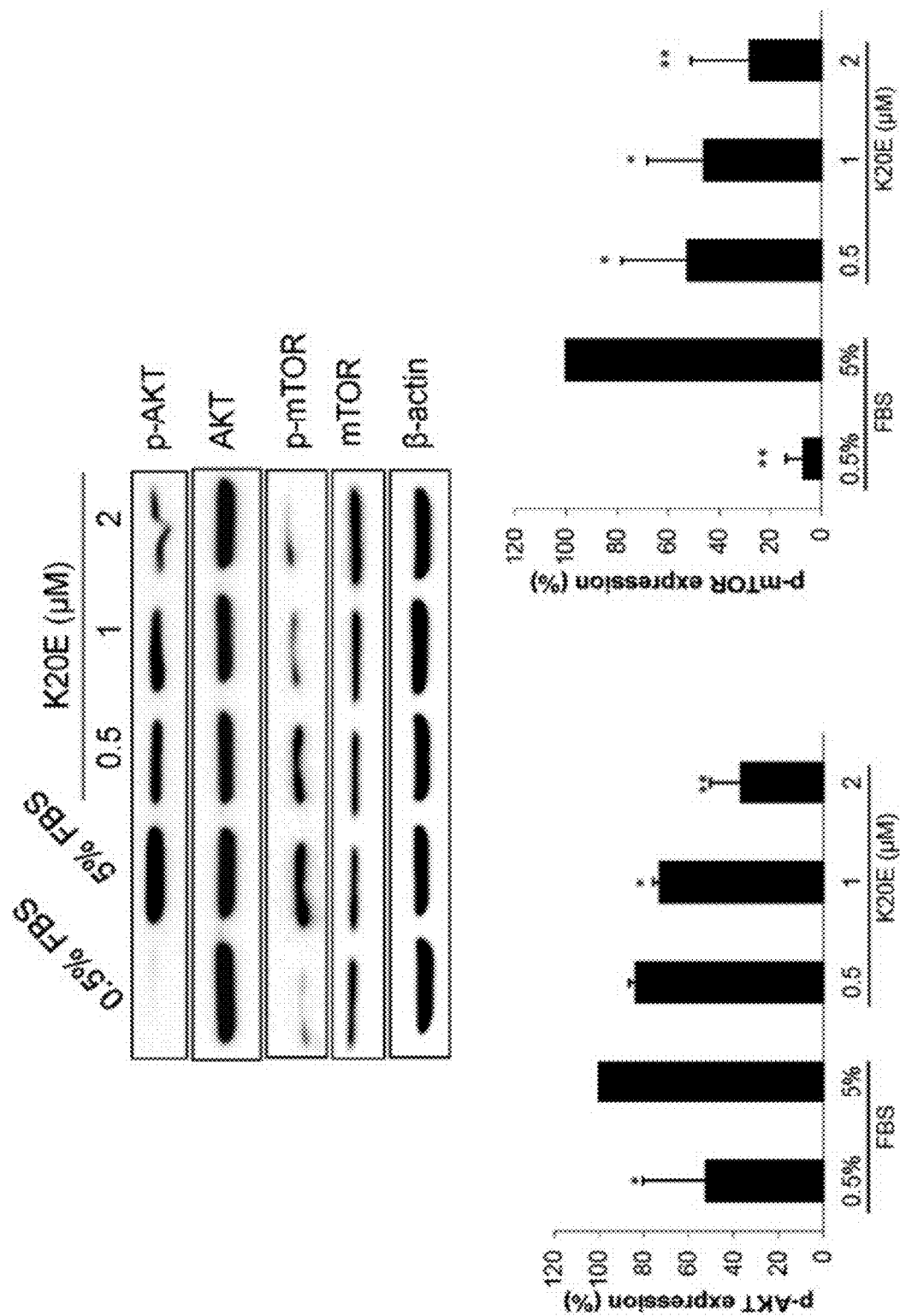
Figure 6D:
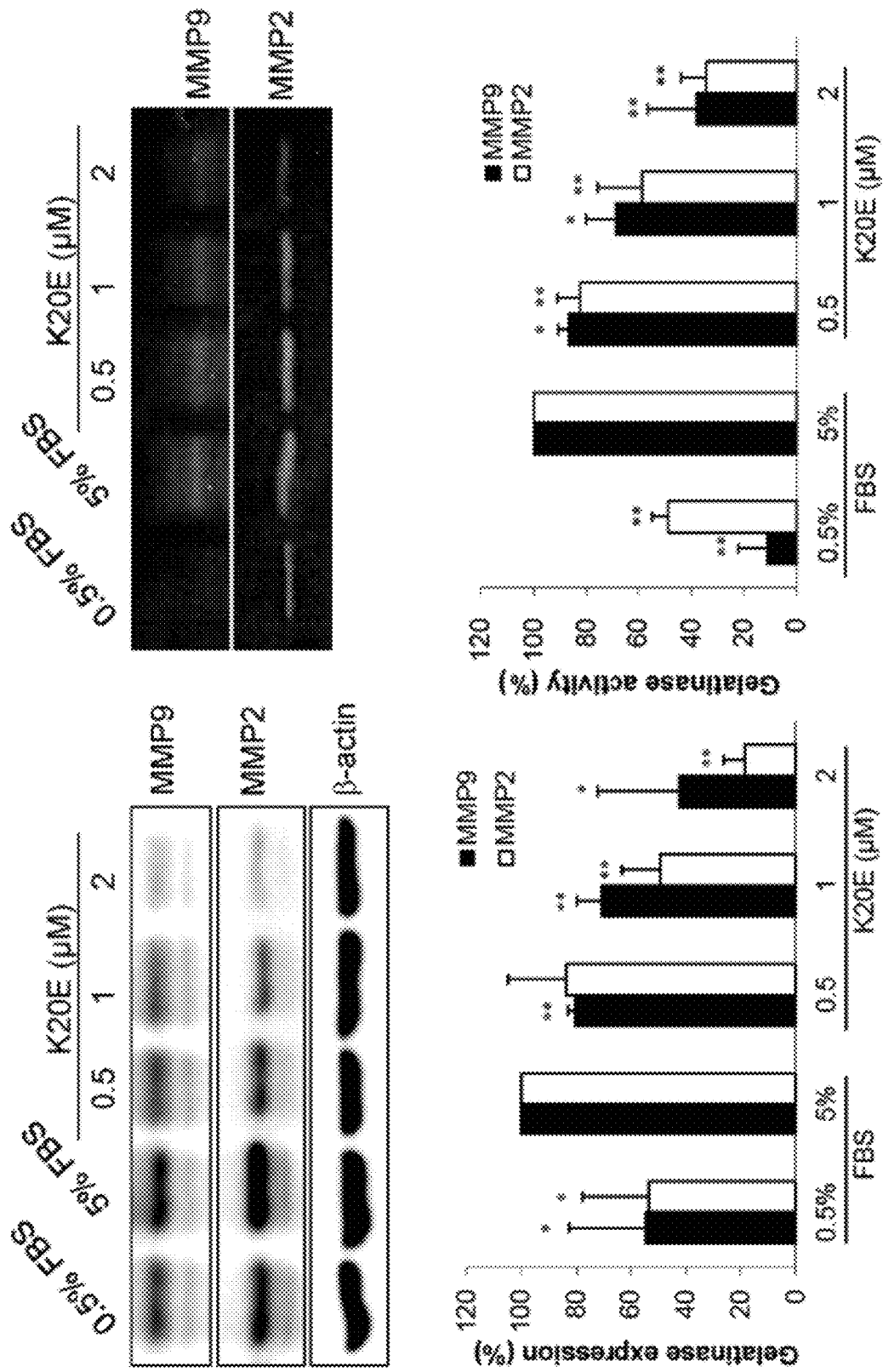

Example 10 K20E Down-Regulated the Expression Levels of VEGF in the LLC1 Cells and VEGFR-2 in the HUVECs VEGF secreted from cancer cells and VEGFR-2 activated on the VECs are two critical processes required for the pathological angiogenesis, including tumor neovascularization. Thereby, the levels of intracellular and secreted VEGF protein were detected within the LLC1 cancer cells and the harvested culture medium, respectively. Our study indicated that K20E can dose-dependently decrease intracellular and secreted levels of VEGF protein in the LLC1 cancer cells (FIG. 5). K20E also markedly down-regulated the expression level of intracellular and surface VEGFR-2 in the HUVECs (FIG. 6A), respectively. Accordingly, the regulatory effect of K20E in the major downstream signaling cascades of VEGFR-2 were further analyzed in the HUVECs. The experimental data revealed that K20E suppressed MEK1/2-ERK1/2 (FIG. 6B) and AKT-mTOR signaling pathway (FIG. 6C) at the activation level rather than total protein level. On the other hand, the protein and activity levels of gelatinases (MMP-2 and MMP-9) that be regulated by MAPK-ERK1/2 and AKT-mTOR signaling cascades were also evidently decreased in the HUVECs treated with K20E (FIG. 6D).

Example 11 K20E Activated the p53-p21 Signaling Pathway in the HUVECs

According to the results obtained from cell cycle distribution analysis, K20E induced the cell cycle arrested at G2/M phase and increased sub-G1 phase in the HUVECs (FIG. 2). Thus, the expression levels of p53-p21 pathway controlling the cell cycle arrest and apoptosis were also analyzed in the present study. The experimental results showed that the expression levels of p53 and p21 proteins were dose-dependently increased in the HUVECs after treatment of K20E (FIG. 7).

What is claimed is:

1. A compound, which is

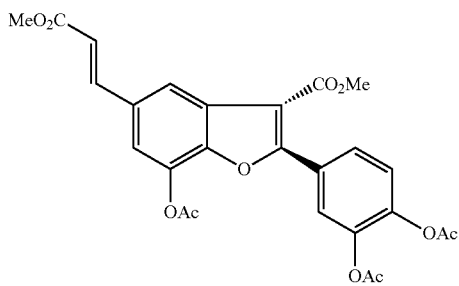

or a stereoisomer thereof, or an enantiomer thereof or a pharmaceutically acceptable salt thereof.

2. A composition comprising a compound of claim 1, or a stereoisomer thereof, or an enantiomer thereof, or a pharmaceutically acceptable salt thereof.

3. A method for treating lung cancer, comprising administering a compound K20E, or a stereoisomer thereof, or an enantiomer thereof, or a pharmaceutically acceptable salt thereof to a subject

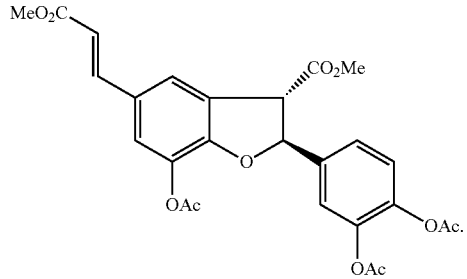

4. A method for inhibiting a lung cancer cell, comprising contacting a compound K20E, or a stereoisomer thereof, or an enantiomer thereof, or a pharmaceutically acceptable salt thereof with the lung cancer cell

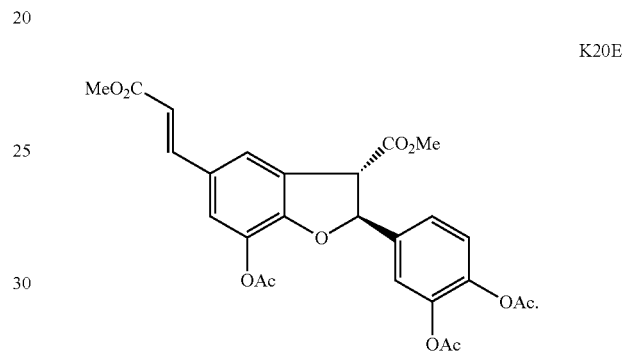

5. The method of claim 4, wherein the cancer cell is a LLC1 cell.

* * * * *